(12) United States Patent
Moussa et al.

(10) Patent No.: US 8,470,870 B2
(45) Date of Patent: Jun. 25, 2013

(54) SOLID FORMS OF AN ANTI-HIV PHOSPHOINDOLE COMPOUND

(75) Inventors: Adel M. Moussa, Burlington, MA (US); Mike H. O'Neill, Painesville, OH (US); Xiaohong Sheng, Beachwood, OH (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 265 days.

(21) Appl. No.: 12/934,627

(22) PCT Filed: Mar. 27, 2009

(86) PCT No.: PCT/US2009/038479
§ 371 (c)(1),
(2), (4) Date: Oct. 29, 2010

(87) PCT Pub. No.: WO2009/120914
PCT Pub. Date: Oct. 1, 2009

(65) Prior Publication Data
US 2011/0039803 A1    Feb. 17, 2011

Related U.S. Application Data

(60) Provisional application No. 61/072,349, filed on Mar. 27, 2008, provisional application No. 61/043,841, filed on Apr. 10, 2008, provisional application No. 61/155,869, filed on Feb. 26, 2009.

(51) Int. Cl.
*A61K 31/404* (2006.01)
*C07D 209/30* (2006.01)

(52) U.S. Cl.
USPC .......................................... 514/419; 548/412

(58) Field of Classification Search
None
See application file for complete search history.

(56) References Cited

U.S. PATENT DOCUMENTS

| 3,798,209 | A | 3/1974 | Witkowski et al. |
| 4,328,245 | A | 5/1982 | Yu et al. |
| 4,409,239 | A | 10/1983 | Yu |
| 4,410,545 | A | 10/1983 | Yu et al. |
| 4,797,286 | A | 1/1989 | Thakkar et al. |
| 4,957,924 | A | 9/1990 | Beauchamp |
| 5,026,687 | A | 6/1991 | Yarchoan et al. |
| 5,372,808 | A | 12/1994 | Blatt et al. |
| 5,433,951 | A | 7/1995 | Serajuddin et al. |
| 5,496,546 | A | 3/1996 | Wang et al. |
| 5,538,865 | A | 7/1996 | Reyes et al. |
| 5,610,054 | A | 3/1997 | Draper |
| 5,633,358 | A | 5/1997 | Gruetzke et al. |
| 5,633,388 | A | 5/1997 | Diana et al. |
| 5,676,942 | A | 10/1997 | Testa et al. |
| 5,725,859 | A | 3/1998 | Omer |
| 5,738,845 | A | 4/1998 | Imakawa |
| 5,738,846 | A | 4/1998 | Greenwald et al. |
| 5,747,646 | A | 5/1998 | Hakimi et al. |
| 5,792,834 | A | 8/1998 | Hakimi et al. |
| 5,830,455 | A | 11/1998 | Valtuena et al. |
| 5,830,905 | A | 11/1998 | Diana et al. |
| 5,834,594 | A | 11/1998 | Hakimi et al. |
| 5,837,257 | A | 11/1998 | Tsai et al. |
| 5,846,964 | A | 12/1998 | Ozeki |
| 5,849,696 | A | 12/1998 | Chretien et al. |
| 5,869,253 | A | 2/1999 | Draper |
| 5,891,874 | A | 4/1999 | Colacino et al. |
| 5,908,621 | A | 6/1999 | Glue et al. |
| 5,922,757 | A | 7/1999 | Chojkier |
| 5,928,636 | A | 7/1999 | Alber et al. |
| 5,942,223 | A | 8/1999 | Bazer et al. |
| 5,980,884 | A | 11/1999 | Blatt et al. |
| 5,990,276 | A | 11/1999 | Zhang et al. |
| 6,004,933 | A | 12/1999 | Spruce et al. |
| 6,034,134 | A | 3/2000 | Gold et al. |
| 6,043,077 | A | 3/2000 | Barber et al. |
| 6,171,615 | B1 | 1/2001 | Roussin et al. |
| 6,350,458 | B1 | 2/2002 | Modi |
| 6,410,531 | B1 | 6/2002 | Llinas-Brunet et al. |
| 6,420,380 | B2 | 7/2002 | Llinas-Brunet et al. |
| 6,534,523 | B1 | 3/2003 | Llinas-Brunet et al. |
| 6,812,219 | B2 | 11/2004 | LaColla et al. |
| 6,825,201 | B2 | 11/2004 | Wang et al. |
| 6,914,054 | B2 | 7/2005 | Sommadossi et al. |
| 7,534,809 | B2 | 5/2009 | Storer et al. |
| 2006/0074054 | A1 | 4/2006 | Storer et al. |
| 2007/0032407 | A1 | 2/2007 | La Colla et al. |
| 2008/0213217 | A1 | 9/2008 | Storer et al. |

FOREIGN PATENT DOCUMENTS

| DE | 19914474 A1 | 10/1999 |
| EP | 1961757 A1 | 8/2008 |
| EP | 1799696 B1 | 11/2008 |
| JP | 10101591 A | 4/1998 |

(Continued)

OTHER PUBLICATIONS

Dalton, Paul, Project Inform, Issue 46, p. 13 (Sep. 2008).*
PCT International Preliminary Report on Patentability and Written Opinion of the International Searching Authority dated Mar. 31, 2009, in International Application No. PCT/US2007/020900, filed Sep. 28, 2007.
PCT International Preliminary Report on Patentability and Written Opinion of the International Searching Authority dated Sep. 28, 2010, in International Application No. PCT/US2009/038479, filed Mar. 27, 2009.
PCT International Search Report dated Apr. 1, 2008, in International Application No. PCT/US2007/020900, filed Sep. 28, 2007.
PCT International Search Report dated Jul. 7, 2009, in International Application No. PCT/US2009/038479, filed Mar. 27, 2009.

(Continued)

*Primary Examiner* — Michael Barker
(74) *Attorney, Agent, or Firm* — Jones Day

(57) ABSTRACT

Solid forms comprising a compound useful in the treatment, prevention and management of various conditions and diseases are provided herein. In particular, provided herein are solid forms comprising (2-carbamoyl-5-chloro-1H-indol-3-yl)-[3-((E)-2-cyano-vinyl)-5-methyl-phenyl]-(R)-phosphinic acid methyl ester, including salts thereof, having utility for the treatment, prevention and management of conditions and disorders including, but not limited to, human immunodeficiency virus infection.

46 Claims, 13 Drawing Sheets

FOREIGN PATENT DOCUMENTS

Figure 1A:
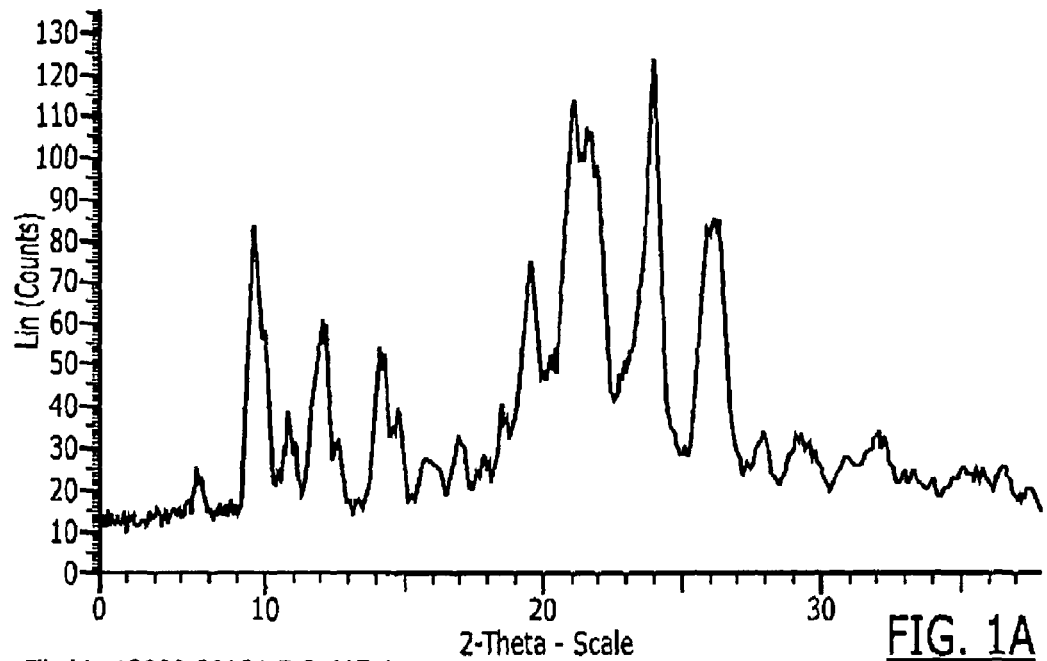

| | | |
|---|---|---|
| WO | WO 95/13090 A1 | 5/1995 |
| WO | WO 97/36554 A1 | 10/1997 |
| WO | WO 98/17679 A1 | 4/1998 |
| WO | WO 98/22496 A2 | 5/1998 |
| WO | WO 99/07734 A2 | 2/1999 |
| WO | WO 99/15194 A1 | 4/1999 |
| WO | WO 99/32139 A1 | 7/1999 |
| WO | WO 99/32140 A1 | 7/1999 |
| WO | WO 99/43691 A1 | 9/1999 |
| WO | WO 99/59621 A1 | 11/1999 |
| WO | WO 99/64016 A1 | 12/1999 |
| WO | WO 00/09531 A2 | 2/2000 |
| WO | WO 00/37110 A2 | 6/2000 |
| WO | WO 01/32153 A2 | 5/2001 |
| WO | WO 01/60315 A2 | 8/2001 |
| WO | WO 01/79246 A2 | 10/2001 |
| WO | WO 01/90121 A2 | 11/2001 |
| WO | WO 01/92282 A2 | 12/2001 |
| WO | WO 01/96353 A2 | 12/2001 |
| WO | WO 02/08187 A1 | 1/2002 |
| WO | WO 02/08198 A2 | 1/2002 |
| WO | WO 02/08251 A2 | 1/2002 |
| WO | WO 02/08256 A2 | 1/2002 |
| WO | WO 02/18404 A2 | 3/2002 |
| WO | WO 02/32414 A2 | 4/2002 |
| WO | WO 02/32920 A2 | 4/2002 |
| WO | WO 02/48116 A2 | 6/2002 |
| WO | WO 02/48157 A2 | 6/2002 |
| WO | WO 02/48165 A2 | 6/2002 |
| WO | WO 02/48172 A2 | 6/2002 |
| WO | WO 02/57287 A2 | 7/2002 |
| WO | WO 02/57425 A2 | 7/2002 |
| WO | WO 02/60926 A2 | 8/2002 |
| WO | WO 03/24461 A1 | 3/2003 |
| WO | WO 2004/00300 A1 | 12/2003 |
| WO | WO 2004/02422 A1 | 1/2004 |
| WO | WO 2004/02999 A2 | 1/2004 |
| WO | WO 2004/14364 A1 | 2/2004 |
| WO | WO 2006/54182 A2 | 5/2006 |
| WO | WO 2007/38796 A1 | 4/2007 |
| WO | WO 2008/42240 A2 | 4/2008 |

OTHER PUBLICATIONS

ISA/EP, PCT Written Opinion of the International Searching Authority dated Apr. 1, 2008, in International Application No. PCT/US2007/020900, filed Sep. 28, 2007.

ISA/EP, PCT Written Opinion of the International Searching Authority dated Jul. 7, 2009, in International Application No. PCT/US2009/038479, filed Mar. 27, 2009.

EPO Communication dated Feb. 11, 2010, in European Application No. 07 838 974.9-2117.

USPTO Non Final Rejection Office Action dated Dec. 11, 2009, in U.S. Appl. No. 11/906,095.

Alt et al., "Specific Inhibition of Hepatitis C Viral Gene Expression by Antisense Phosphorothioate Oligodeoxynucleotides," *Hepatology*, Sep. 1995, 22(3):707-17.

Alt et al., "Core specific antisense phosphorothioate oligodeoxynucleotides as potent and specific inhibitors of hepatitis C viral translation," *Archives of Virology*, 1997, 142:589-99.

Attwood et al., "The design and synthesis of potent inhibitors of hepatitis C virus NS3-4A proteinase," *Antivir. Chem. & Chemother.*, 1999 10:259-73.

Bhat et al., "Oral Session V: Hepatitis C Virus, Flaviviruses; Synthesis and Pharmacokinetic Properties of Nucleoside Analogues as Possible Inhibitors of HCV RNA Replication," *Antivir. Res.*, Feb. 2003, 57(3):A75 (16th International Conference on Antiviral Research Abstract 120).

Chu et al, "Structure of Sch 68631: A New Hepatitis C Virus Proteinase Inhibitor from *Streptomyces* sp," *Tetrahedron Letters*, 1996, 37(40):7229-32.

Chu et al., "Isolation and Structure of Sch 351633: A Novel Hepatitis C Virus (HCV) NS3 Protease Inhibitor From the Fungus *Penicillium griseofulvum*," *Bioorganic & Medicinal Chem. Letts.*, 1999, 9:1949-52.

Davis, "Current Therapy for Chronic Hepatitis C," *Gastroenterology*, Feb. 2000(Supp.), 118(2):S104-14.

De Francesco et al., "Approaching a new era for hepatitis C virus therapy: inhibitors of the NS3-4A serine protease and the NS5B RNA-dependent RNA polymerase," *Antivir. Res.*, vol. 58:1-16. (2002).

Dymock et al., "Novel approaches to the treatment of hepatitis C virus infection," *Antivir. Chem. & Chemother.*, Mar. 2000 11(2):79-96.

Ferrari et al., "Characterization of Soluble Hepatitis C Virus RNA-Dependent RNA Polymerase Expressed in *Escherichia coli*," *J. Virology*, Feb. 1999, 73(2):1649-54.

Galderisi et al., "Antisense Oligonucleotides as Therapeutic Agents," *J. of Cellular Physiology*, 1999, 181:251-257.

Hastead, "Selective Primary Health Care: Strategies for Control of Disease in the Developing World," *Reviews Infect. Dis.*, Mar.-Apr. 1994, 6(2):251-64.

Kakiuchi et al., "Non-peptide inhibitors of HCV serine proteinase," *FEBS Letters*, 1998, 421:217-220.

Lohmann et al., "Biochemical and Kinetic Analyses of NS5B RNA-Dependent RNA Polymerase of the Hepatitis C Virus," *Virology*, 1998, 249:108-118.

Macejak et al., "Inhibition of Viral Replication by Nuclease Resistant Hammerhead Ribozymes Directed Against Hepatitis C Virus RNA," *Hepatology*, Oct. 1999, 30(4)(Pt. 2):409A (AASLD Abstract 995).

Meyers et al, "Molecular Characterization of Pestiviruses," *Adv. Virus Res.*, 1996, 47:53-118.

Moennig et al., "The Pestiviruses," *Adv. Vir. Res.*, 1992, 41:53-98.

Monath, "Japanese Encephalitis—A Plague of the Orient," *N. Engl. J. Med.*, Sep. 8, 1988, 319(10):641-43.

Qasim et al., "Interscaffolding Additivity. Association of $P_1$ Variants of Eglin c and of Turkey Ovomucoid Third Domain with Serine Proteinases," *Biochemistry*, 1997 36(7):1598-1607.

Olsen et al., "Oral Session V: Hepatitis C Virus, Flaviviruses; 2'—Modified Nucleoside Analogs as Inhibitors of Hepatitis C RNA Replication," *Antivir. Res.*, Feb. 2003, 57(3):A76 (16th International Conference on Antiviral Research Abstract 121).

Sudo et al., "Establishment of an in vitro assay system for screening hepatitis C virus protease inhibitors using high performance liquid chromatography," *Antivir. Res.*, 1996, 32:9-18.

Sudo et al, "Novel Hepatitis C Virus Protease Inhibitors: Thiazolidine Derivatives," *Biochem. & Biophys. Res. Comm.*, 1997, 238(2):643-47.

Sudo et al., "Novel hepatitis C virus protease inhibitors: 2,4,6-trihydroxy,3-nitro-benzamide derivatives," *Antivir. Chem. & Chemother.*, Mar. 1998, 9(2):186 (Erratum to *Antivir. Chem. & Chemother.*, 8(6):541-44).

Takeshita et al., "An Enzyme-Linked Immunosorbent Assay for Detecting Proteolytic Activity of Hepatitis C Virus Proteinase," *Analytical Biochem.*, 1997, 247:242-46.

\* cited by examiner

SOLID FORMS OF AN ANTI-HIV PHOSPHOINDOLE COMPOUND

1. CROSS-REFERENCE TO RELATED APPLICATIONS

This application is a National Stage of International Application No. PCT/US2009/038479, filed Mar. 27, 2009, which claims the benefit of U.S. Provisional Patent Applications 61/072,349 filed Mar. 27, 2008, 61/043,841 filed Apr. 10, 2008, and 61/155,869 filed Feb. 26, 2009, the contents of each of which applications are incorporated herein by reference in their entireties.

2. FIELD

Provided herein are solid forms comprising stereomerically or enantiomerically pure (2-carbamoyl-5-chloro-1H-indol-3-yl)-[3-((E)-2-cyano-vinyl)-5-methyl-phenyl]-(R)-phosphinic acid methyl ester or a salt thereof. Also provided herein are pharmaceutical compositions comprising the solid forms, methods of making the solid forms, and methods of their use for the treatment of various diseases and/or disorders.

3. BACKGROUND

Indoles, nucleosides and their analogues have been used in the treatment of viral infections in mammals, including humans. Viruses that infect mammals and are treatable by the administration of pharmaceutical compositions comprising indoles, nucleosides or their analogues or derivatives include hepatitis C virus (HCV), human immunodeficiency virus (HIV), pestiviruses, and flaviviruses (Moennig et al., *Adv. Vir. Res.* 1992, 41:53-98; Meyers and Thiel, *Adv. In Viral Res.* 1996, 47:53-118; Moennig et al., *Adv. Vir. Res.* 1992, 41:53-98; Halstead, *Rev. Infect. Dis.* 1984, 6:251-64; Halstead, *Science* 1988, 239:476-81; Monath, *New Engl. J. Med.* 1988, 319:641-3).

PCT Publication No. WO 2004/014364 to Idenix Pharmaceuticals discloses a class of phenylindoles that display enhanced anti-HIV activity. These compounds are substituted with at least two moieties on the phenyl ring and/or the benzo ring of the indole functionality. In addition, these compounds incorporate a number of substituents having a carboxamide functionality at position-2 on the indole group of the compounds.

Idenix Pharmaceuticals also disclosed another class of phenylindole compounds, including phosphophenylindoles, for the treatment of HIV and/or AIDS (US 2006/0074054 and WO 06/054182).

In light of the fact that HIV infections have reached epidemic levels worldwide and have tragic effects on infected hosts, there remains a strong need to provide new and effective pharmaceutical agents, but with low toxicity, to treat these viral infections.

4. SUMMARY

Provided herein are solid forms, including amorphous forms and crystal forms, comprising (2-carbamoyl-5-chloro-1H-indol-3-yl)-[3-((E)-2-cyano-vinyl)-5-methyl-phenyl]-(R)-phosphinic acid methyl ester (I):

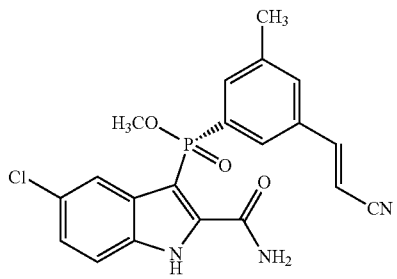

or a salt thereof.

In certain embodiments, provided herein are crystal forms of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are polymorphs of crystal forms of (2-carbamoyl-5-chloro-1H-indol-3-yl)-[3-((E)-2-cyano-vinyl)-5-methyl-phenyl]-(R)-phosphinic acid methyl ester.

Provided herein are both hydrous and anhydrous crystal forms of (2-carbamoyl-5-chloro-1H-indol-3-yl)-[3-((E)-2-cyano-vinyl)-5-methyl-phenyl]-(R)-phosphinic acid methyl ester or a salt thereof. In certain embodiments, provided herein are anhydrous crystal forms of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are polymorphs of anhydrous crystal forms of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are solvates of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are polymorphs of solvates of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are hydrates of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are polymorphs of hydrates of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are monohydrates of (2-carbamoyl-5-chloro-1H-indol-3-yl)-[3-((E)-2-cyano-vinyl)-5-methyl-phenyl]-(R)-phosphinic acid methyl ester. In certain embodiments, provided herein are polymorphs of monohydrates of (2-carbamoyl-5-chloro-1H-indol-3-yl)-[3-((E)-2-cyano-vinyl)-5-methyl-phenyl]-(R)-phosphinic acid methyl ester.

In certain embodiments, provided herein are amorphous solid forms of (2-carbamoyl-5-chloro-1H-indol-3-yl)-[3-((E)-2-cyano-vinyl)-5-methyl-phenyl]-(R)-phosphinic acid methyl ester.

In certain embodiments, provided herein are crystal forms of a mixture of R and S isomers of (2-carbamoyl-5-chloro-1H-indol-3-yl)-[3-((E)-2-cyano-vinyl)-5-methyl-phenyl]phosphinic acid methyl ester. In certain embodiments, provided herein are crystal forms of a racemic mixture of R and S isomers of (2-carbamoyl-5-chloro-1H-indol-3-yl)-[3-((E)-2-cyano-vinyl)-5-methyl-phenyl]phosphinic acid methyl ester. In certain embodiments, provided herein are polymorphs of crystal forms of a mixture of R and S isomers of (2-carbamoyl-5-chloro-1H-indol-3-yl)-[3-((E)-2-cyano-vinyl)-5-methyl-phenyl]phosphinic acid methyl ester. In certain embodiments, provided herein are polymorphs of crystal forms of a racemic mixture of R and S isomers of (2-carbamoyl-5-chloro-1H-indol-3-yl)-[3-((E)-2-cyano-vinyl)-5-methyl-phenyl]phosphinic acid methyl ester.

Also provided herein are pharmaceutical compositions comprising the solid forms. In certain embodiments, provided herein are pharmaceutical compositions comprising a solid form, including a crystal form, a crystalline salt form, a polymorph of a salt form, a solvate of a salt form, a hydrate of a salt form, or an amorphous form as provided herein; and/or a pharmaceutically acceptable diluent, excipient, or carrier.

Furthermore, provided herein are methods of their use for the treatment, prevention, and/or management of conditions and disorders, including, but not limited to, pestivirus infection, flavivirus infection, hepacivirus infection, and human immunodeficiency virus infection. In certain embodiments, provided herein are methods for the treatment, prevention, and/or management of one or more of the following conditions or disorders: pestivirus infection, flavivirus infection, hepacivirus infection, and human immunodeficiency virus infection, wherein such methods comprise administering to a subject, e.g., a human, in need of such treatment, prevention, and/or management a therapeutically and/or prophylactically effective amount of a solid form provided herein. In certain embodiments, provided herein are methods for the treatment, prevention, and/or management of conditions and disorders including, but not limited to, pestivirus infection, flavivirus infection, hepacivirus infection, and human immunodeficiency virus infection, comprising administering to a subject, e.g., a human, in need of such treatment, prevention or management and/or and prophylactically effective amount of a solid form provided herein.

In addition, provided are methods of making, isolating, and/or characterizing the solid forms provided herein.

In certain embodiments, the solid forms provided herein are useful as active pharmaceutical ingredients for the preparation of formulations for use in animals or humans. In certain embodiments, provided herein is the use of these solid forms as a final drug product. In certain embodiments, the solid forms, including crystal forms, amorphous forms, and final drug products provided herein are useful, for example, for the treatment, prevention or management of conditions and disorders listed above.

5. BRIEF DESCRIPTION OF THE FIGURES

Figure 1B:
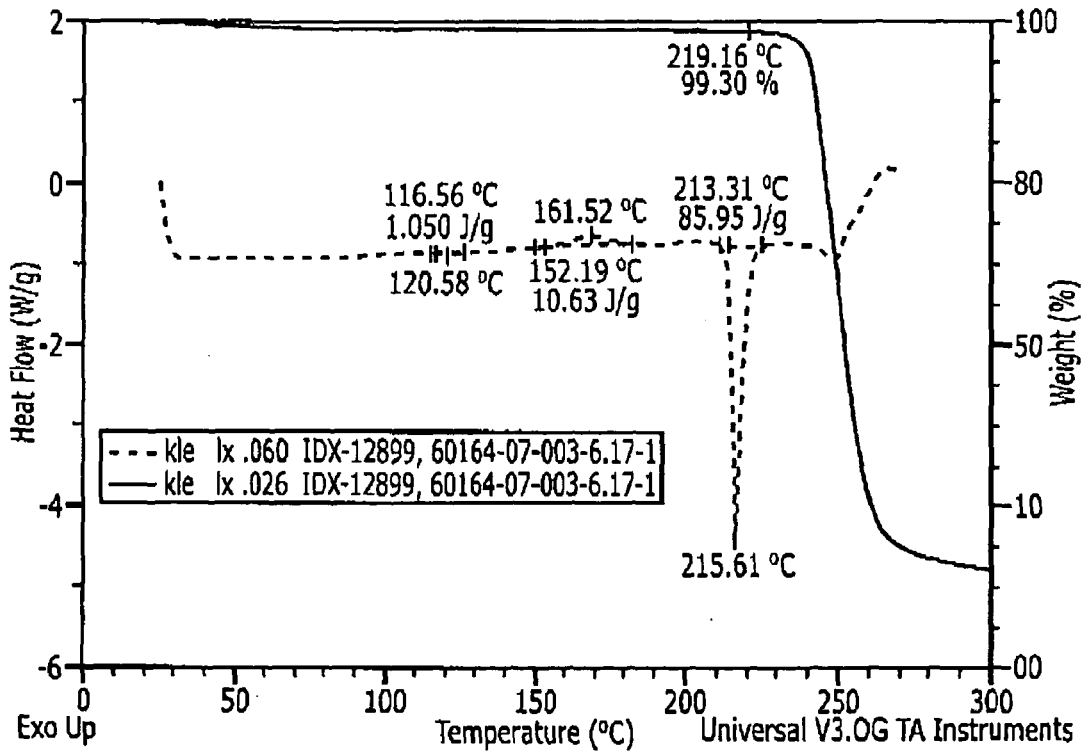
Figure 1C:
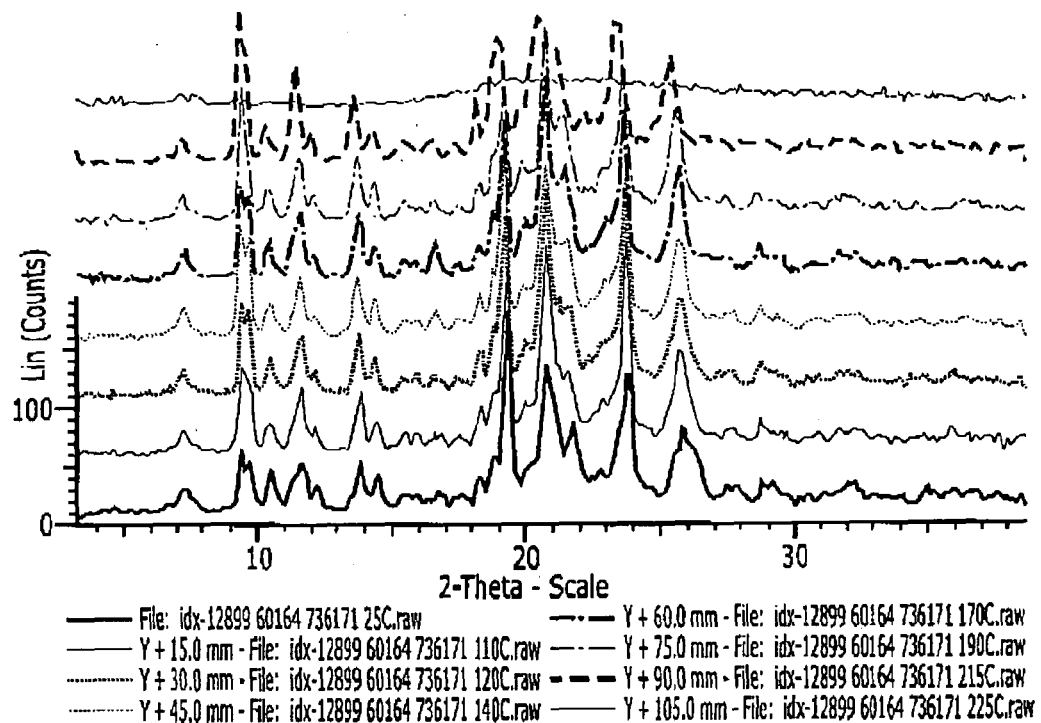
Figure 2A:
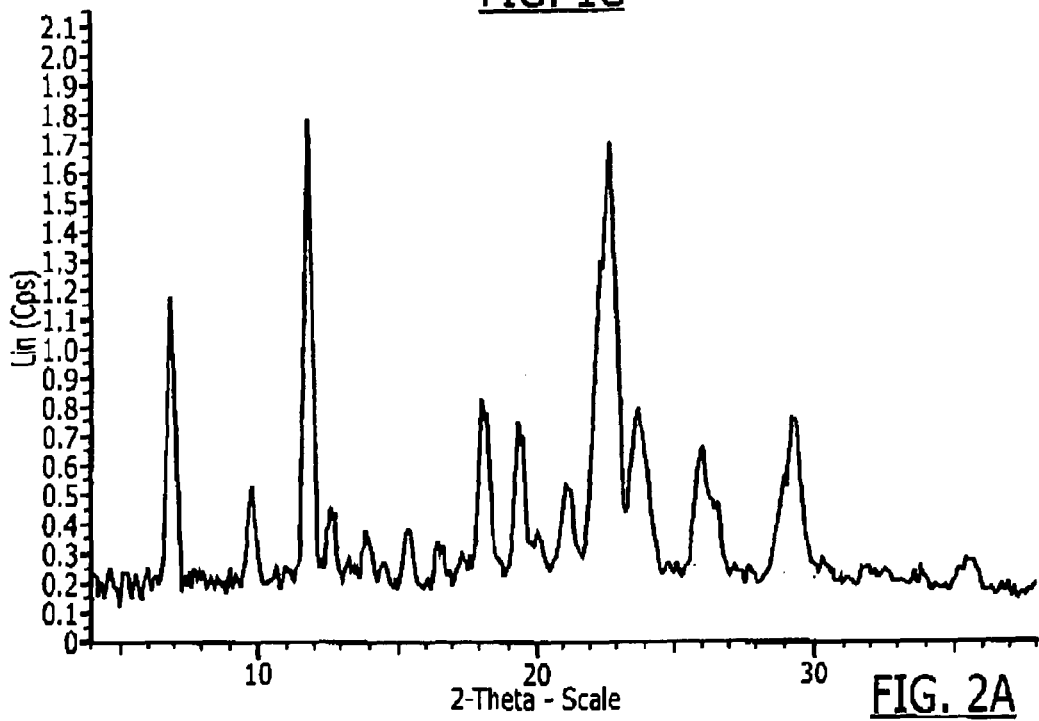
Figure 2B:
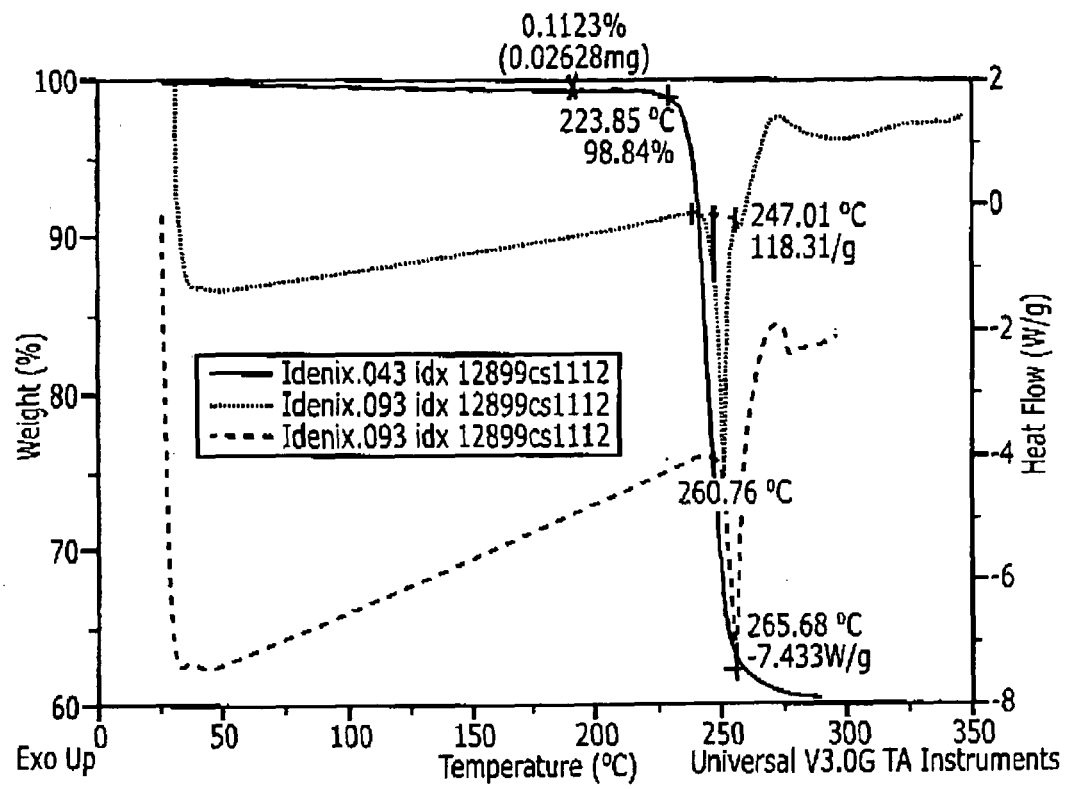
Figure 3A:
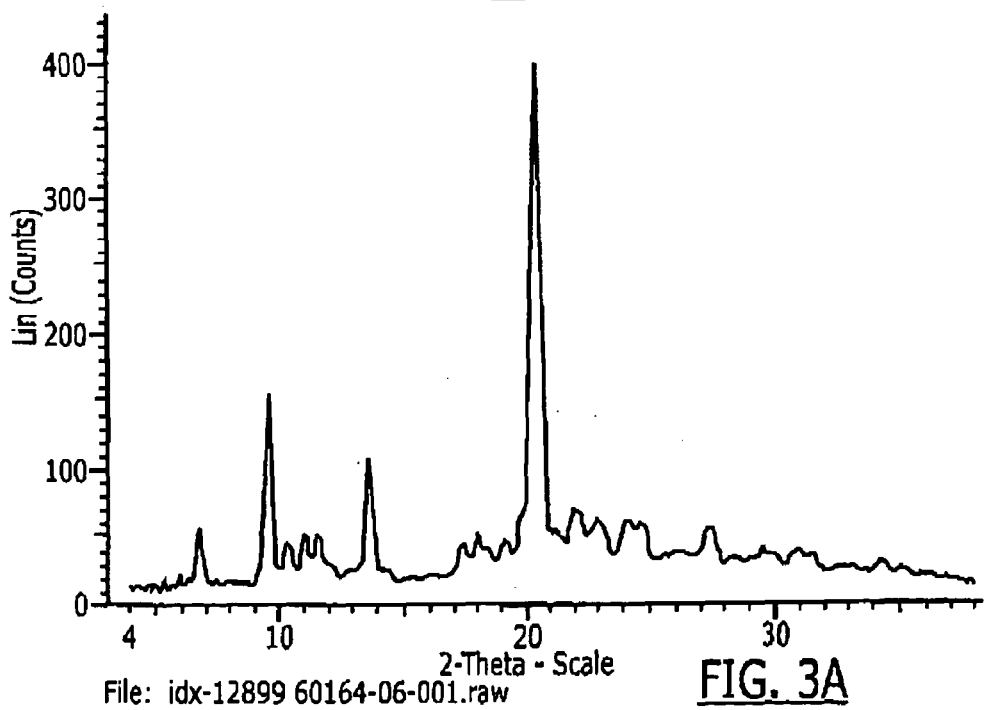
Figure 3B:
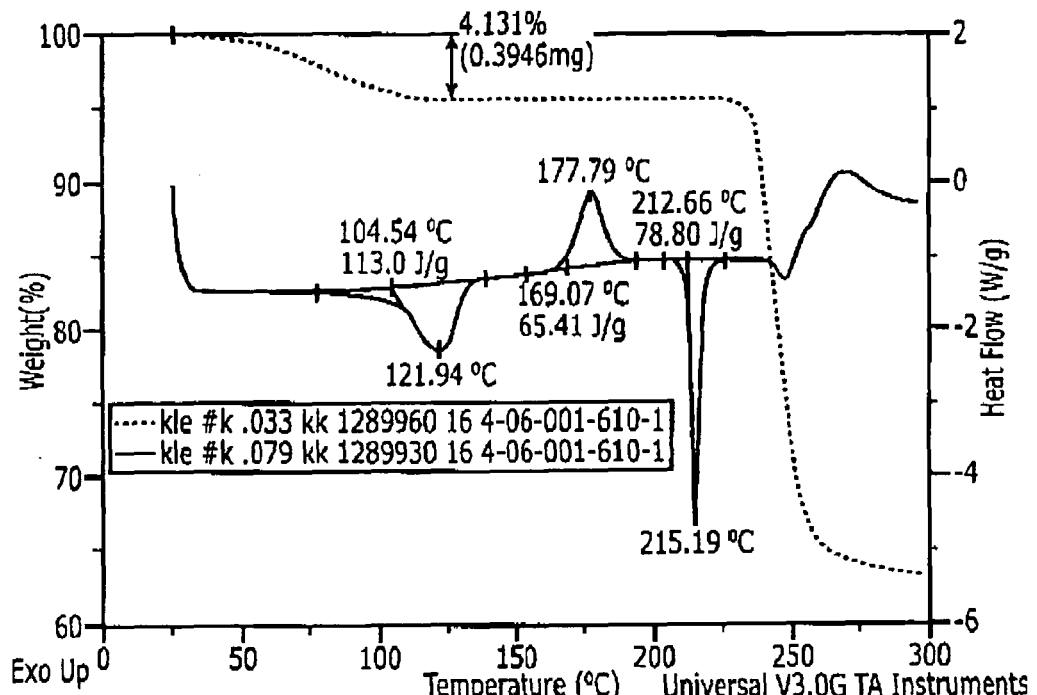
Figure 3C:
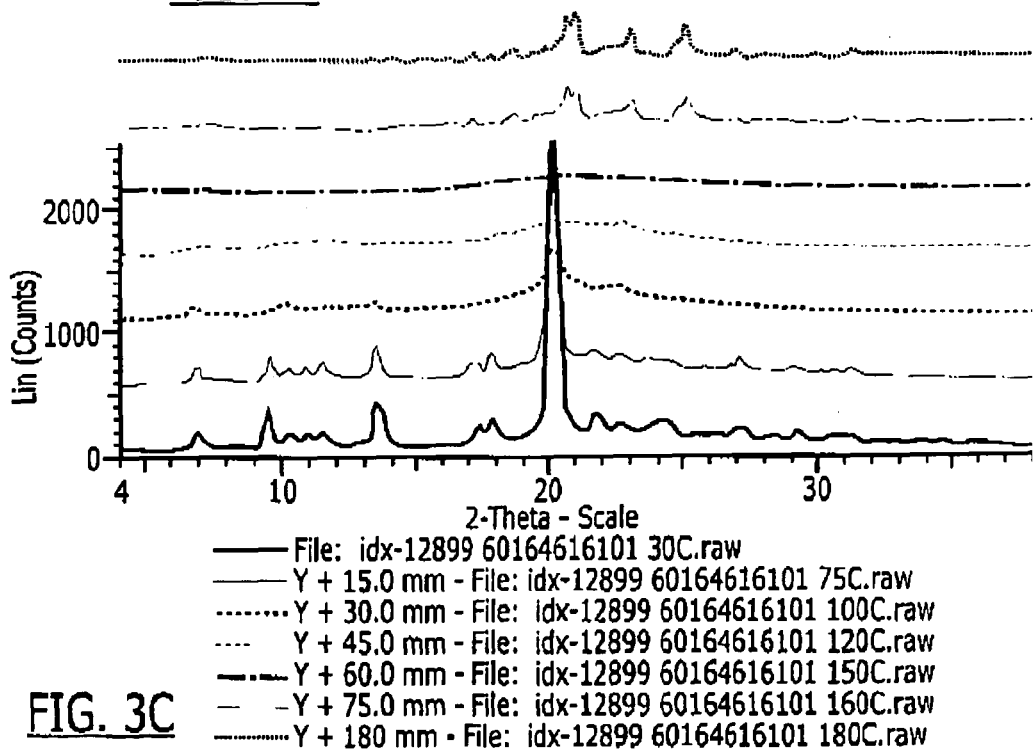
Figure 4A:
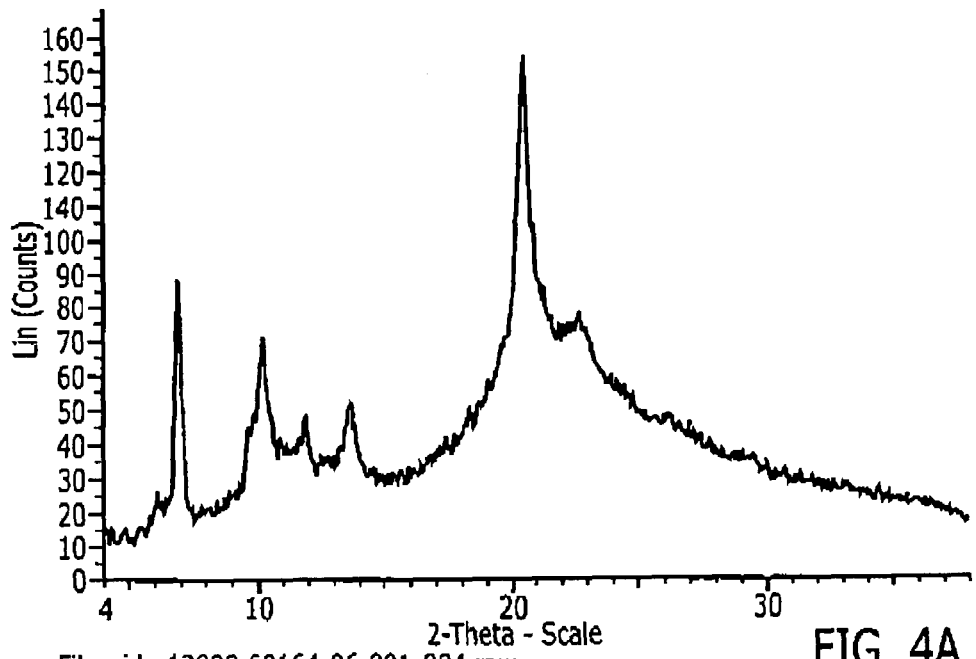
Figure 4B:
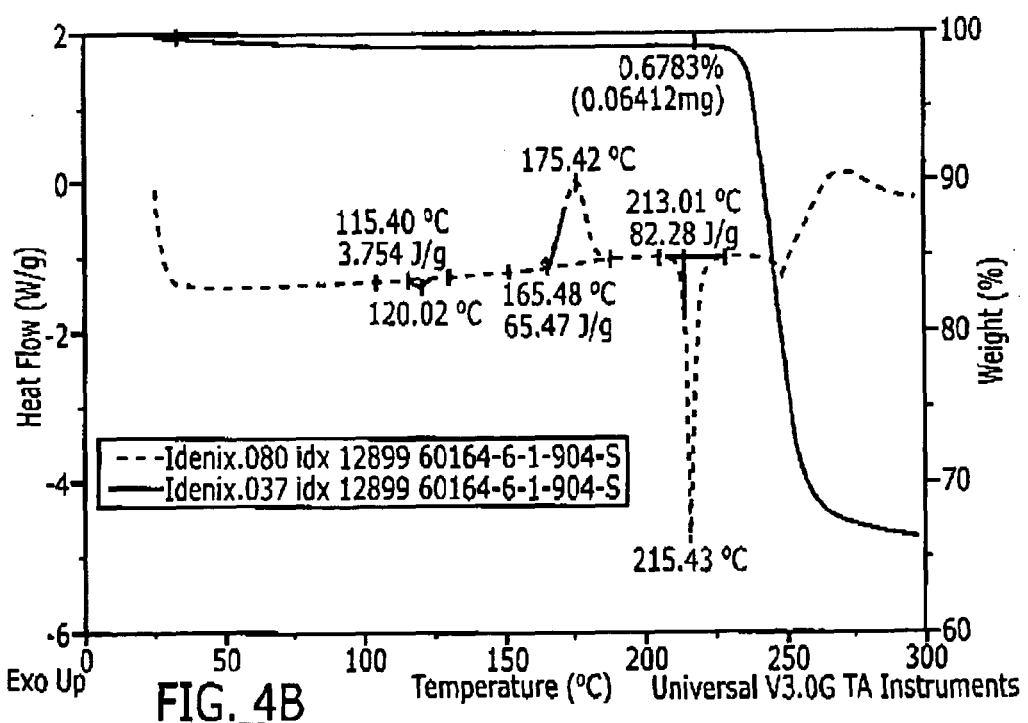
Figure 4C:
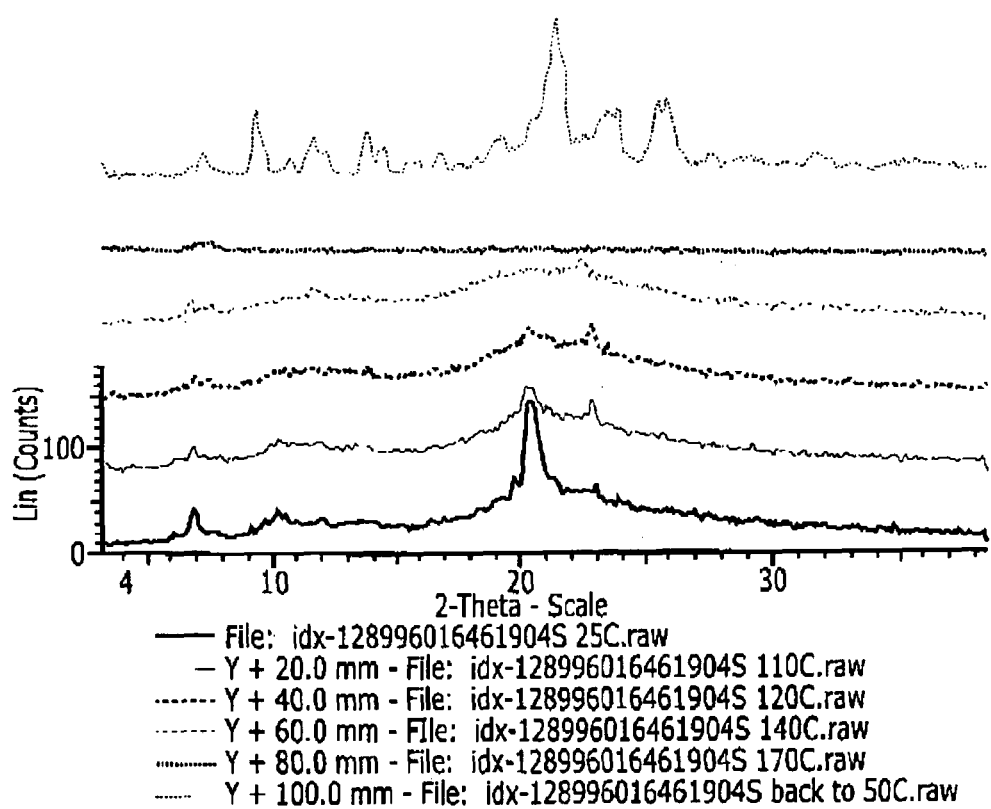
Figure 5:
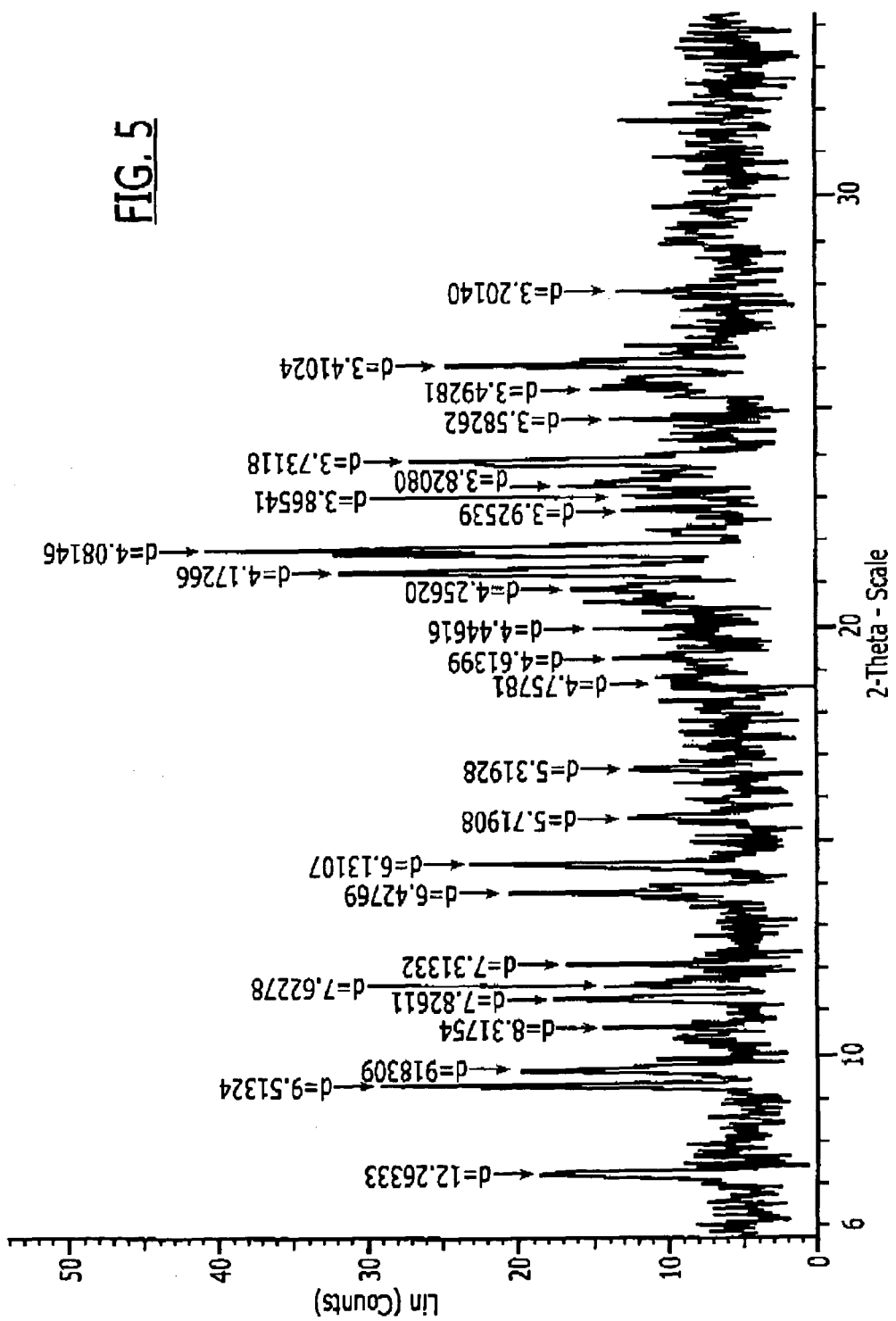
Figure 6:
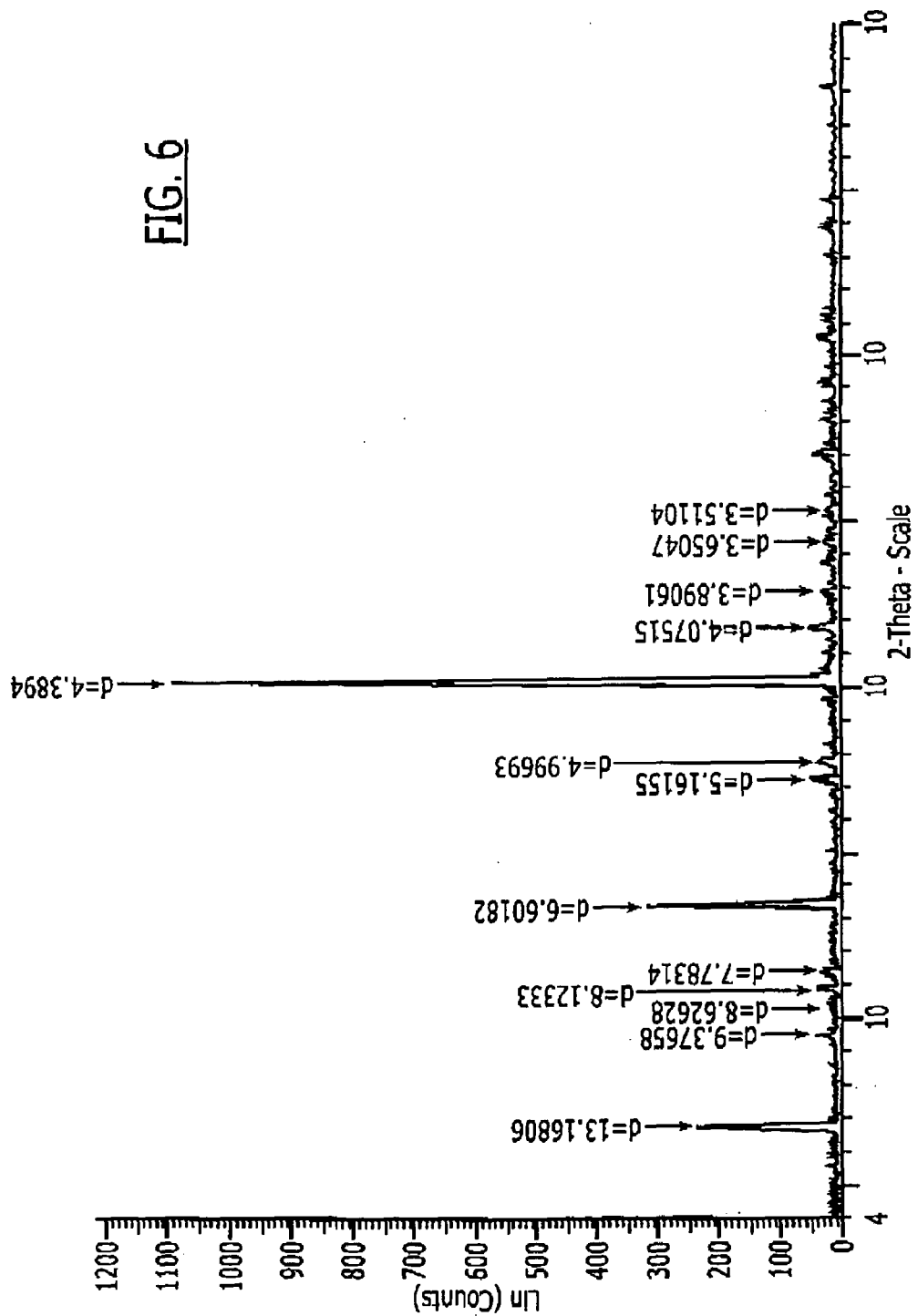
Figure 7:
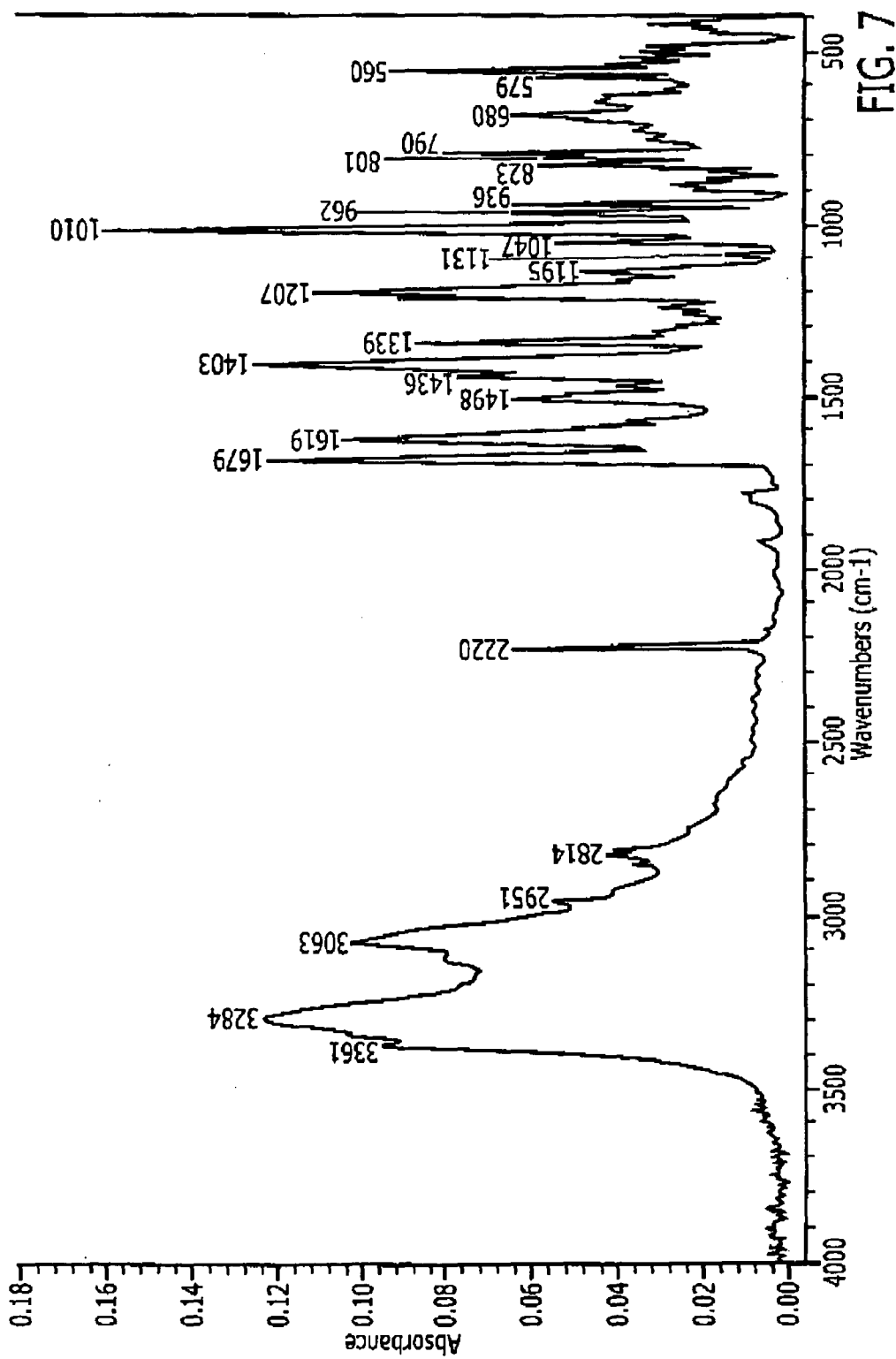
Figure 8:
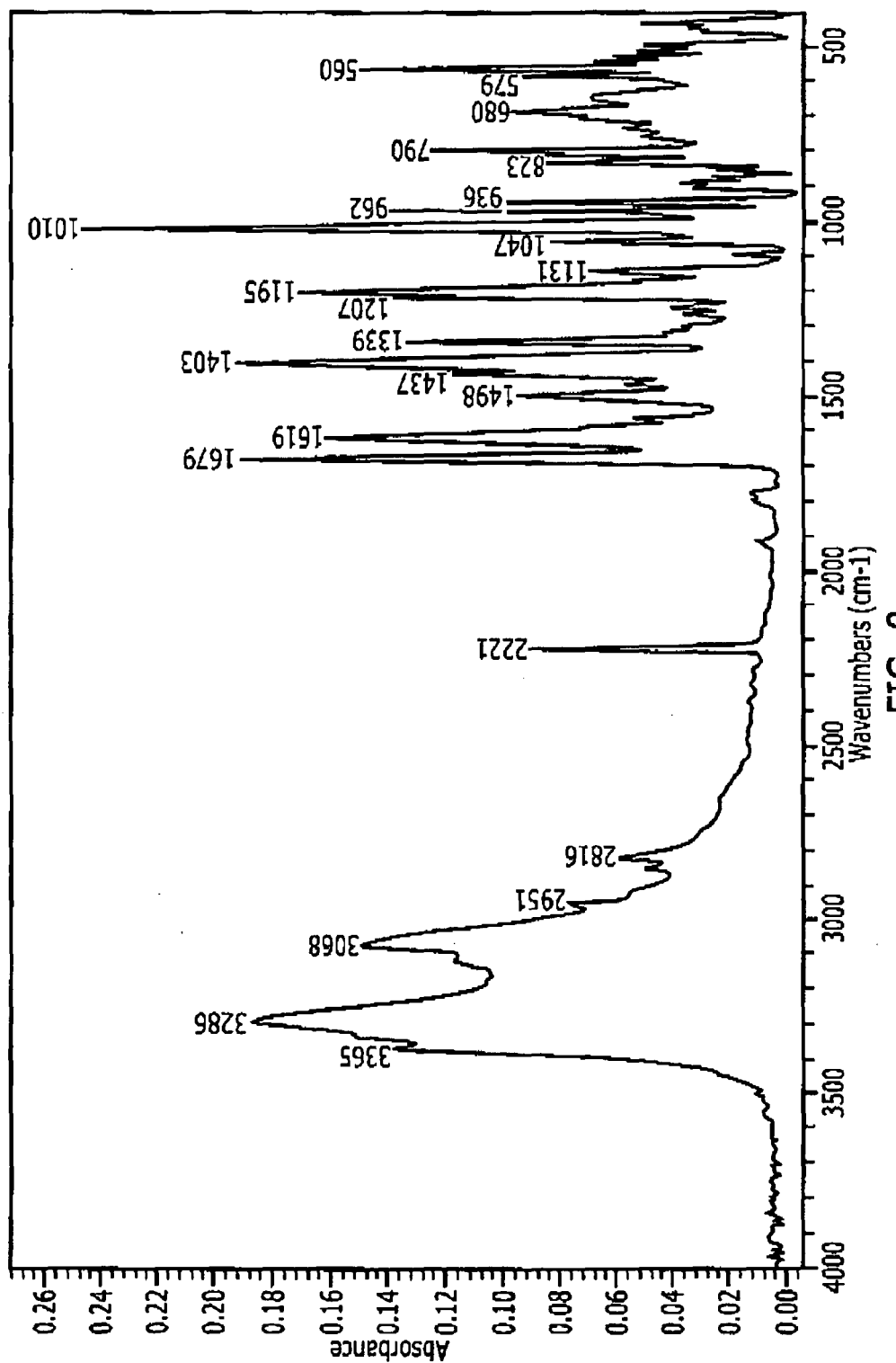
Figure 9:
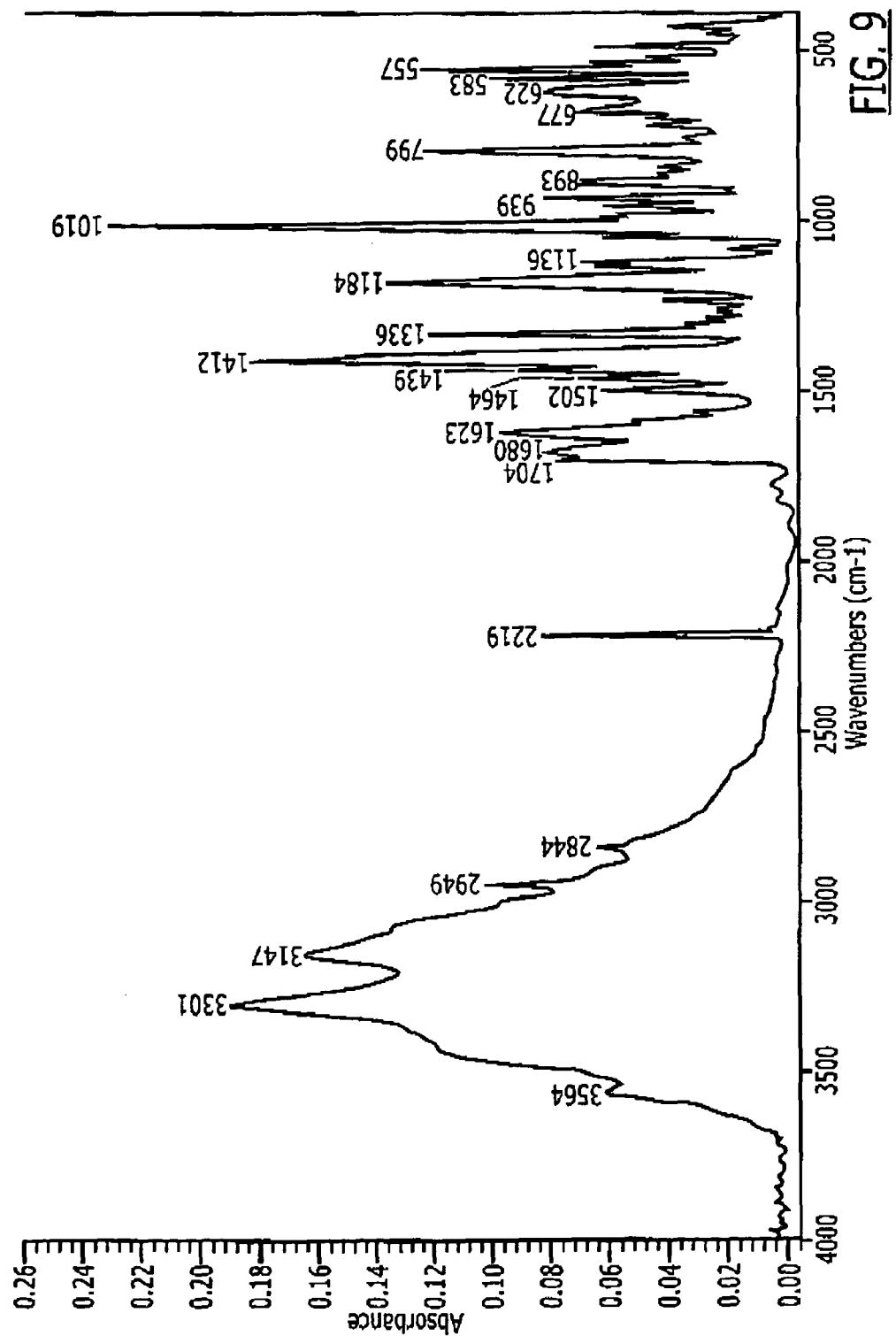
Figure 10:
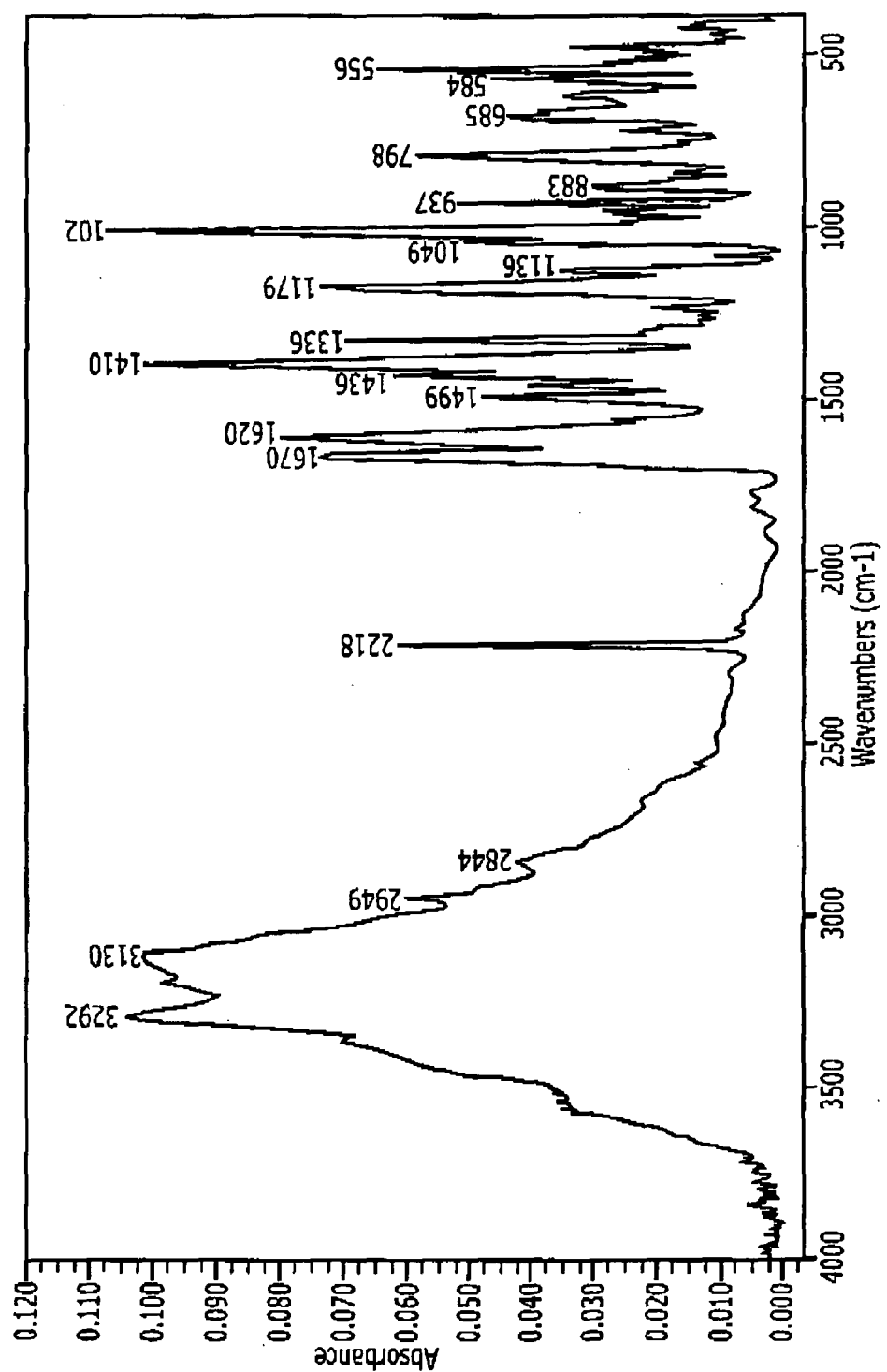
Figure 11:
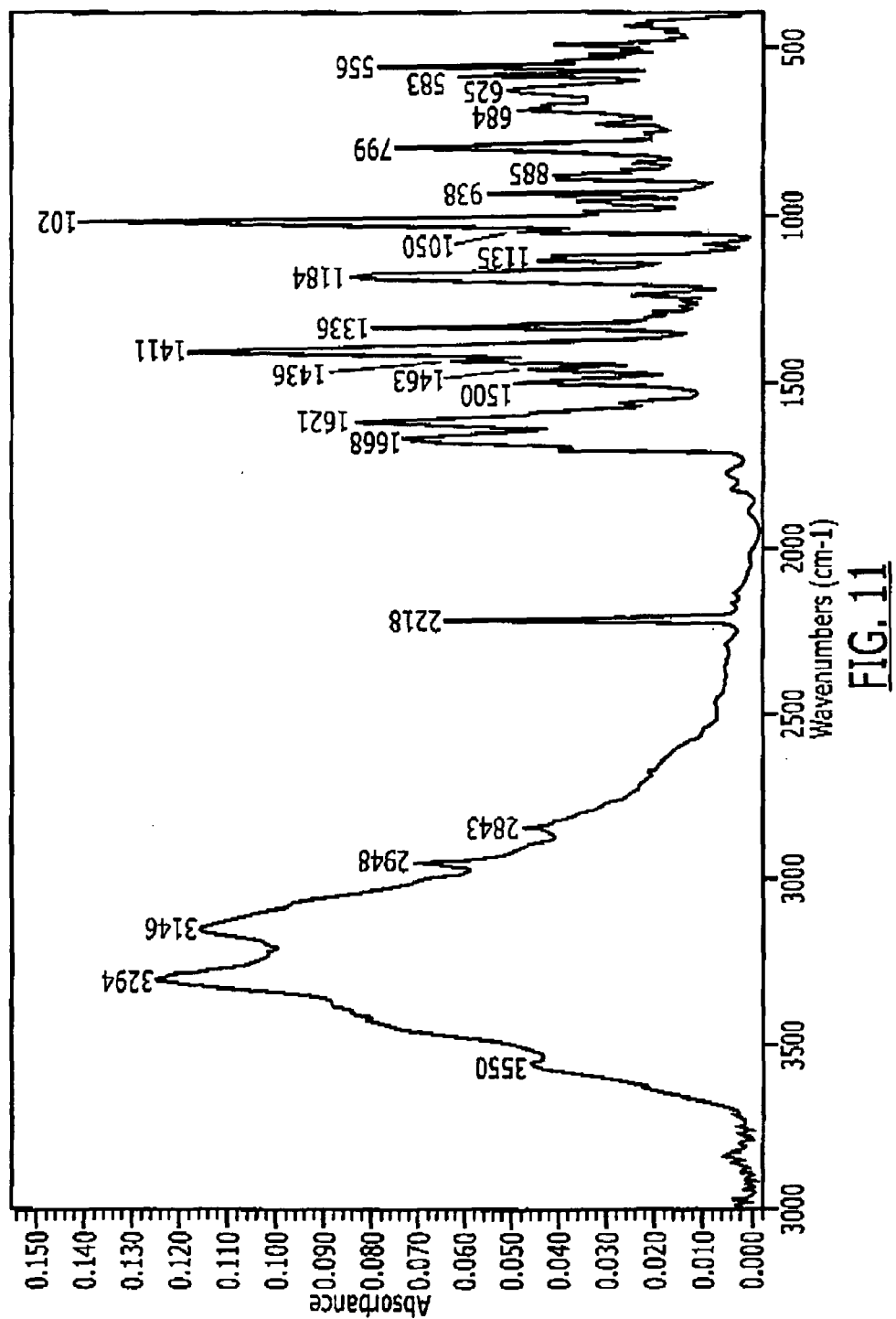

FIG. 1A provides an X-ray powder diffraction of Form I;
FIG. 1B provides a DSC-TGA overlay of Form I;
FIG. 1C provides a variable temperature X-ray powder diffraction of Form I;
FIG. 2A provides an X-ray powder diffraction of Form IX;
FIG. 2B provides a DSC-TGA overlay of Form IX;
FIG. 3A provides an X-ray powder diffraction of Form VIII;
FIG. 3B provides a DSC-TGA overlay of Form VIII;
FIG. 3C provides a variable temperature X-ray powder diffraction of Form VIII.
FIG. 4A provides an X-ray powder diffraction of Form III;
FIG. 4B provides a DSC-TGA overlay of Form III; and
FIG. 4C provides a variable temperature X-ray powder diffraction of Form III.
FIG. 5 provides an X-ray powder diffraction pattern of Form I.
FIG. 6 provides an X-ray powder diffraction pattern of Form VIII.
FIG. 7 provides an infrared spectrum of Form I.
FIG. 8 provides an infrared spectrum of Form I.
FIG. 9 provides an infrared spectrum of Form VIII.
FIG. 10 provides an infrared spectrum of Form VIII.
FIG. 11 provides an infrared spectrum of Form VIII.

6. DETAILED DESCRIPTION

Provided herein are compositions of matter, methods of use, and pharmaceutical compositions for the treatment of virus infections, e.g., HIV infections, in mammals. In certain embodiments, provided herein are solid forms of (2-carbamoyl-5-chloro-1H-indol-3-yl)-[3-((E)-2-cyano-vinyl)-5-methyl-phenyl]-(R)-phosphinic acid methyl ester, compositions comprising these solid forms, and methods of use of the solid forms and compositions for the treatment or prophylaxis of an infection in a host. In addition, provided herein are processes for the preparation of the solid forms.

6.1 Definitions

As used herein the term "pure," when applied to a chiral compound, refers to an enantiomer of the chiral compound substantially free from its opposite enantiomer (i.e., in enantiomeric excess). For example, the pure "R" form of a compound is substantially free from the "S" form of the compound and is, thus, in enantiomeric excess of the "R" form. The term "enantiomerically pure" or "pure enantiomer" denotes that the compound comprises an excess of an enantiomer, e.g., more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight, or more than 99.9% by weight of the enantiomer. In certain embodiments, the weights are based upon total weight of the compound, i.e., all enantiomers of the compound. In certain embodiments, one enantiomer can be in excess by 30-80%, 30-70%, 30-60%, 30%, 35%, 40%, 45%, 50%, 55% or 60%, or any percentage in between.

As used herein and unless otherwise indicated, the term "enantiomerically pure (R)-compound" refers, e.g., to at least about 80% by weight (R)-compound and at most about 20% by weight (S)-compound, at least about 90% by weight (R)-phosphoindole and at most about 10% by weight (S)-compound, at least about 95% by weight (R)-compound and at most about 5% by weight (S)-compound, at least about 99% by weight (R)-compound and at most about 1% by weight (S)-compound, or at least about 99.9% by weight (R)-compound and at most about 0.1% by weight (S)-compound. In certain embodiments, the weights are based upon total weight of the compound, i.e., both or all of the enantiomers of the compound.

In the compositions provided herein, an enantiomerically pure compound, or a pharmaceutically acceptable salt, solvate, hydrate, ester, or prodrug thereof, can be present with other active or inactive ingredients. For example, a pharmaceutical composition comprising an enantiomerically pure (R)-compound can comprise, for example, about 90% of an excipient and about 10% of the enantiomerically pure (R)-compound. In certain embodiments, the enantiomerically pure (R)-compound in such compositions can, for example, comprise, at least about 99.9% by weight of the (R)-compound and at most about 0.1% by weight of the (S)-compound. In certain embodiments, the active ingredient can be formulated with little or no carrier, excipient, or diluent.

The term "chiral" as used herein includes a compound that has the property that it is not superimposable on its mirror image.

The term "isolated" includes a composition that includes at least 85%, 90%, 95%, 98%, 99%, or 100% by weight of a desired compound.

As used herein, a crystalline or amorphous form that is "pure," i.e., substantially free of other crystalline or amorphous forms, contains less than about 10%, less than about 5%, less than about 3%, or less than about 1% by weight of one or more other crystalline or amorphous form.

As used herein and unless otherwise indicated, a composition that is "substantially free" of a compound means that the composition contains less than about 20%, less than about 10%, less than about 5%, less than about 3%, or less than about 1% by weight of the compound.

The term "solid forms" and related terms used herein, unless otherwise specified, refer to crystal forms and amorphous forms, comprising (2-carbamoyl-5-chloro-1H-indol-3-yl)-[3-((E)-2-cyano-vinyl)-5-methyl-phenyl]-(R)-phosphinic acid methyl ester, and specifically includes crystal forms and amorphous forms of (2-carbamoyl-5-chloro-1H-indol-3-yl)-[3-((E)-2-cyano-vinyl)-5-methyl-phenyl]-(R)-phosphinic acid methyl ester.

The term "crystalline" and related terms used herein, when used to describe a substance, component, or product, mean that the substance, component, or product is crystalline as determined by X-ray diffraction. See, e.g., *Remington's Pharmaceutical Sciences*, 18$^{th}$ ed., Mack Publishing, Easton Pa., 173 (1990); *The United States Pharmacopeia*, 23$^{rd}$ ed., 1843-1844 (1995).

The term "crystal forms" and related terms herein refer to the various crystalline modifications of a given substance, including, but not limited to, polymorphs, solvates, hydrates, co-crystals, and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates, such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

The terms "polymorphs," "polymorphic forms," and related terms herein refer to two or more crystal forms that are composed of the same molecule, molecules, or ions. Different polymorphs may have different physical properties, such as, for example, melting temperatures, heats of fusion, solubilities, dissolution rates, and/or vibrational spectra as a result of the arrangement or conformation of the molecules or ions in the crystal lattice (see, e.g., Byrn, Pfeiffer, and Stowell, (1999) Solid-State Chemistry of Drugs, 2nd ed., SSCI, Inc.: West Lafayette, Ind.). The differences in physical properties exhibited by polymorphs affect pharmaceutical parameters, such as storage stability, compressibility, and density (important in formulation and product manufacturing); and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

The term "solvate" and "solvated," as used herein, refer to a crystal form of a substance which contains a solvent. The term "hydrate" and "hydrated" refer to a solvate wherein the solvent is water. "Polymorphs of solvates" refers to the existence of more than one crystal form for a particular solvate composition. Similarly, "polymorphs of hydrates" refers to the existence of more than one crystal form for a particular hydrate composition.

The term "amorphous," "amorphous form," and related terms used herein mean that the material, substance, component, or product under consideration is not crystalline as determined by X-ray diffraction. Amorphous forms of a substance can be obtained by a number of methods, as known in the art. Such methods include, but are not limited to, heating, melt cooling, rapid melt cooling, solvent evaporation, rapid solvent evaporation, desolvation, sublimation, grinding, cryo-grinding, and freeze drying.

Techniques for characterizing crystal forms and amorphous forms include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state NMR, optical microscopy, hot stage optical microscopy, scanning electron microscopy (SEM), electron crystallography and quantitative analysis, particle size analysis (PSA), surface area analysis, solubility studies, and dissolution studies.

The term "host," as used herein, refers to a unicellular or multicellular organism in which a virus can replicate, including cell lines and animals, and in certain instances, a human. Alternatively, a host can be carrying a part of the HIV viral genome, whose replication or function can be altered by the solid forms provided herein. In certain embodiments, the term host specifically refers to infected cells, cells transfected with all or part of the HIV genome and animals, in particular, primates (including chimpanzees) and humans. In certain embodiments, the host is a human patient. Veterinary applications, in certain indications, however, are clearly encompassed by embodiments provided herein (such as chimpanzees).

The term "subject" is defined herein to include animals such as mammals, including, but not limited to, primates (e.g., humans), cows, sheep, goats, horses, dogs, cats, rabbits, rats, mice, and the like. In certain embodiments, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "$IC_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21*st Edition*; Lippincott Williams & Wilkins: Philadelphia, Pa., 2005; *Handbook of Pharmaceutical Excipients,* 5*th Edition*; Rowe et al., Eds., The Pharmaceutical Press and the American Pharmaceutical Association: 2005; and *Handbook of Pharmaceutical Additives,* 3*rd Edition*; Ash and Ash Eds., Gower Publishing Company: 2007; *Pharmaceutical Preformulation and Formulation,* Gibson Ed., CRC Press LLC: Boca Raton, Fla., 2004).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the terms "about" and "approximately," when used in connection with a numeric value or range of values which is provided to describe a particular solid form, e.g., a specific temperature or temperature range, such as, for example, that describing a melting, dehydration, desolvation, or glass transition; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary by 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of the recited value or range of values while still describing the particular solid form.

6.2 Embodiments

In certain embodiments, provided herein are solid forms comprising stereomerically pure (2-carbamoyl-5-chloro-1H-indol-3-yl)-[3-((E)-2-cyano-vinyl)-5-methyl-phenyl]-(R)-phosphinic acid methyl ester or a salt thereof, including solvated and hydrated forms thereof, and amorphous forms; pharmaceutical compositions comprising the solid forms alone or in combination with other active ingredients; methods of their use in the treatment, prevention, and/or management of conditions and disorders, including, but not limited to, pestivirus infection, flavivirus infection, hepacivirus infection, and human immunodeficiency virus infection. While not intending to be bound by any particular theory, the storage stability, compressibility, density, or dissolution properties of the solid forms can be beneficial for manufacturing, formulation, and pharmacokinetic properties (e.g., bio-availability) of (2-carbamoyl-5-chloro-1H-indol-3-yl)-[3-((E)-2-cyano-vinyl)-5-methyl-phenyl]-(R)-phosphinic acid methyl ester or a salt thereof, including solvated and hydrated forms thereof.

In certain embodiments, solid forms provided herein are those that are characterized by physical properties, e.g., stability, solubility, and dissolution rate, appropriate for clinical and therapeutic dosage forms. Certain solid forms provided herein are characterized by physical properties, e.g., crystal morphology, compressibility, and hardness, suitable for manufacture of a solid dosage form. Such properties can be determined using techniques such as X-ray diffraction, microscopy, IR spectroscopy, and thermal analysis, as described herein or known in the art.

In certain embodiments, also provided herein are crystal forms comprising stereomerically or enantiomerically pure (2-carbamoyl-5-chloro-1H-indol-3-yl)-[3-((E)-2-cyano-vinyl)-5-methyl-phenyl]-(R)-phosphinic acid methyl ester or a salt thereof. In certain embodiments, those crystal forms have utility for the treatment, prevention, or management of conditions and disorders, including, but not limited to, pestivirus infection, flavivirus infection, hepacivirus infection, and human immunodeficiency virus infection. In certain embodiments, the solid forms provided herein are crystal forms comprising (2-carbamoyl-5-chloro-1H-indol-3-yl)-[3-((E)-2-cyano-vinyl)-5-methyl-phenyl]-(R)-phosphinic acid methyl ester.

In certain embodiments, crystal forms provided herein can be made by crystallization of (2-carbamoyl-5-chloro-1H-indol-3-yl)-[3-((E)-2-cyano-vinyl)-5-methyl-phenyl]-(R)-phosphinic acid methyl ester. In certain embodiments, (2-carbamoyl-5-chloro-1H-indol-3-yl)-[3-((E)-2-cyano-vinyl)-5-methyl-phenyl]-(R)-phosphinic acid methyl ester is dissolved in a solvent or a mixture of solvents to form a solution, and then crystallized from the solution to yield crystal forms provided herein. Exemplary methods of making crystal forms provided herein are described below.

In one embodiment, provided herein is Form I, an anhydrous crystal form of (2-carbamoyl-5-chloro-1H-indol-3-yl)-[3-((E)-2-cyano-vinyl)-5-methyl-phenyl]-(R)-phosphinic acid methyl ester. In certain embodiments, Form I has a thermal gravimetric analysis thermogram substantially similar to that provided in FIG. 1B. In certain embodiments, when examined by thermal gravimetric analysis, Form I has a weight loss corresponding to no greater than about 1.0% of the total mass when heated from about 25° C. to about 219° C. In certain embodiments, when examined by thermal gravimetric analysis, Form I has a weight loss corresponding to between about 0.5% and about 1.0% of the total mass when heated from about 25° C. to about 219° C. In certain embodiments, when examined by thermal gravimetric analysis, Form I has a weight loss corresponding to 0.7% of the total mass when heated from about 25° C. to about 219° C. In certain embodiments, Form I has a differential scanning calorimetry thermogram substantially similar to that provided in FIG. 1B.

In certain embodiments, when examined by differential scanning calorimetry, Form I has one or more of the following thermal events: an endotherm with onset temperature of about 116° C., an endotherm with onset temperature of about 213 C, and an exotherm with onset temperature of about 153° C. In certain embodiments, Form I has an X-ray powder diffraction pattern substantially similar to that provided in FIG. 1A or FIG. 5, using Cu Kα radiation (e.g., 1.5406 angstrom, 40 kV, 40 mA). In certain embodiments, Form I has an X-ray powder diffraction pattern peak at about 21.8° 2θ using Cu Kα radiation. In certain embodiments, Form I has X-ray powder diffraction pattern peaks at one, two, three, four, five, six, seven, or more of the X-ray powder diffraction pattern peak positions provided in FIG. 1A, FIG. 5, and/or Table 2 as provided herein, using Cu Kα radiation. In certain embodiments, Form I has X-ray powder diffraction pattern peaks at about 9.3, about 21.3, about 21.8, about 23.8, and about 26.1° 2θ using Cu Kα radiation. In certain embodiments, Form I has X-ray powder diffraction pattern peaks at about 9.3, about 19.2, about 20.0, about 21.8, about 23.8, and about 26.1° 2θ using Cu Kα radiation. In certain embodiments, Form I has X-ray powder diffraction pattern peaks at about 9.3, about 12.1, about 14.4, about 19.2, about 20.0, about 21.8, about 23.8, and about 26.1° 2θ using Cu Kα radiation. In certain embodiments, Form I has an IR spectrum similar to that depicted in FIG. 7 or FIG. 8. In certain embodiments, Form I has IR peaks at one, two, three, four, five, six, seven, or more of the positions indicated in FIG. 7, FIG. 8, and/or Table 13 as provided herein. In certain embodiments, Form I has one, two, three, or four IR peaks at the following approximate positions: about 3284, about 3063, about 1619, and about 1010 cm$^{-1}$.

In certain embodiments, Form I has advantageous stability. In certain embodiments, Form I has advantageous reproducibility.

Form I of (2-carbamoyl-5-chloro-1H-indol-3-yl)-[3-((E)-2-cyano-vinyl)-5-methyl-phenyl]-(R)-phosphinic acid methyl ester can be made by methods described herein or any method apparent to those of skill in the art. In certain embodiments, Form I is prepared by crystallization of (2-carbamoyl-5-chloro-1H-indol-3-yl)-[3-((E)-2-cyano-vinyl)-5-methyl-phenyl]-(R)-phosphinic acid methyl ester from a solvent system containing one or more solvents, including, but not limited to, methanol, ethanol, 2-propanol, 1-propanol, 2-butanol, 1-butanol, nitromethane, acetonitrile, methylene chloride, chloroform, isopropyl ether, ethyl acetate, isopropyl acetate, methyl ethyl ketone, methyl tert butyl ether (MTBE), water, and mixtures thereof. In certain embodiments, the solvent is an alcoholic solvent, for example, ethanol or methanol. In certain embodiments, Form I is obtained by crystal form conversion from another crystal or amorphous form of (2-carbamoyl-5-chloro-1H-indol-3-yl)-[3-((E)-2-cyano-vinyl)-5-methyl-phenyl]-(R)-phosphinic acid methyl ester, for instance, via a solvent-mediated and/or water-mediated form conversion process. In certain embodiments, Form I is crystallized by dissolving (2-carbamoyl-5-chloro-1H-indol-3-yl)-[3-((E)-2-cyano-vinyl)-5-methyl-phenyl]-(R)-phosphinic acid methyl ester in methanol to form a solution, and adding water as an antisolvent to the solution to cause the compound to crystallize out of solution. In certain embodiments, the methanol is in excess of water, and in one embodiment, the ratio of methanol versus water is 3 to 2. The crystals are then washed with the same methanol water solution. If an excess of water over methanol is used then Form VIII may form.

In another embodiment, provided herein is Form VIII, a monohydrate crystal form of (2-carbamoyl-5-chloro-1H-indol-3-yl)-[3-((E)-2-cyano-vinyl)-5-methyl-phenyl]-(R)-phosphinic acid methyl ester. In certain embodiments, the water is present in the approximate ratio of 1 molar equivalents of water per mole of (2-carbamoyl-5-chloro-1H-indol-3-yl)-[3-((E)-2-cyano-vinyl)-5-methyl-phenyl]-(R)-phosphinic acid methyl ester. In terms of mass, this equates to a water content of approximately 4% of the total mass of a sample of Form VIII. In certain embodiments, the water content of Form VIII ranges from about 3% to about 5% of the total mass of Form VIII. In certain embodiments, Form VIII has a thermal gravimetric analysis thermogram substantially similar to that provided in FIG. 3B. In certain embodiments, when examined by thermal gravimetric analysis, Form VIII has a weight loss of between about 3% and about 5% of the total mass when heated from about 25° C. to about 120° C. In certain embodiments, when examined by thermal gravimetric analysis, Form VIII has a weight loss of about 4% of the total mass when heated from about 25° C. to about 120° C. In certain embodiments, Form VIII has a differential scanning calorimetry thermogram substantially similar to that provided in FIG. 3B. In certain embodiments, when examined by differential scanning calorimetry, Form VIII has endotherms with onset temperatures of about 105 and 213° C. and an exotherm with an onset temperature of about 169° C. In certain embodiments, Form VIII has an X-ray powder diffraction pattern substantially similar to that of FIG. 3A or FIG. 6, using Cu Kα radiation (e.g., 1.5406 angstrom, 40 kV, 40 mA). In certain embodiments, Form VIII has an X-ray powder diffraction pattern peak at about 20.2° 2θ using Cu Kα radiation. In certain embodiments, Form VIII has X-ray powder diffraction pattern peaks at one, two, three, four, five, six, seven, or more of the X-ray powder diffraction pattern positions provided in FIG. 3A, FIG. 6, and/or Table 3 as provided herein, using Cu Kα radiation. In certain embodiments, Form VIII has X-ray powder diffraction pattern peaks at about 6.7, about 9.4, about 13.4, about 20.2, and about 21.8° 2θ, using Cu Kα radiation. In certain embodiments, Form VIII has an IR spectrum substantially similar to that depicted in FIG. 9, FIG. 10, or FIG. 11. In certain embodiments, Form VIII has IR peaks at one, two, three, four, five, six, seven, or more of the positions indicated in FIG. 9, FIG. 10, FIG. 11, and/or Table 13 as provided herein. In certain embodiments, Form VIII has IR peaks at one, two, three, or four of the following approximate positions: about 3301, about 3147, about 1623, and about 1019 cm$^{-1}$.

Form VIII of (2-carbamoyl-5-chloro-1H-indol-3-yl)-[3-((E)-2-cyano-vinyl)-5-methyl-phenyl]-(R)-phosphinic acid methyl ester can be made by methods described herein or any method apparent to those of skill in the art. In certain embodiments, Form VIII is prepared by crystallization of (2-carbamoyl-5-chloro-1H-indol-3-yl)-[3-((E)-2-cyano-vinyl)-5-methyl-phenyl]-(R)-phosphinic acid methyl ester from a solvent system containing one or more solvents, including, but not limited to, 1-butanol, pyridine, acetone, isopropyl acetate, acetonitrile, methylene chloride, toluene, isopropyl ether, dimethylformamide, ethanol, methanol, and mixtures thereof. In certain embodiments, Form VIII is obtained by crystal form conversion from another crystal or amorphous form of (2-carbamoyl-5-chloro-1H-indol-3-yl)-[3-((E)-2-cyano-vinyl)-5-methyl-phenyl]-(R)-phosphinic acid methyl ester, for instance, via a solvent-mediated and/or water-mediated form conversion process.

In yet another embodiment, provided herein is Form IX, an anhydrous crystal form of a mixture of R and S isomers of (2-carbamoyl-5-chloro-1H-indol-3-yl)-[3-((E)-2-cyano-vinyl)-5-methyl-phenyl]phosphinic acid methyl ester. In certain embodiments, Form IX is a racemic mixture of (2-carbamoyl-5-chloro-1H-indol-3-yl)-[3-((E)-2-cyano-vinyl)-5- methyl-phenyl]phosphinic acid methyl ester. In certain embodiments, Form IX has a thermal gravimetric analysis thermogram substantially similar to that provided in FIG. 2B. In certain embodiments, when examined by thermal gravimetric analysis, Form IX has a weight loss of no greater than 1% of the total mass when heated from about 25° C. to about 200° C. In certain embodiments, when examined by thermal gravimetric analysis, Form IX has a weight loss of between about 0.3% and about 0.5% of the total mass when heated from about 25° C. to about 200° C. In certain embodiments, when examined by thermal gravimetric analysis, Form IX has a weight loss of about 0.4% of the total mass when heated from about 25° C. to about 200° C. In certain embodiments, Form IX has a differential scanning calorimetry thermogram substantially similar to that provided in FIG. 2B. In certain embodiments, when examined by differential scanning calorimetry, Form IX has no thermal events between about 25 and 247° C. In certain embodiments, when examined by differential scanning calorimetry, Form IX has an exotherm with an onset temperature of about 247° C. In certain embodiments, Form IX has an X-ray powder diffraction pattern substantially similar to that provided FIG. 2A using Cu Kα radiation (e.g., 1.5406 angstrom, 40 kV, 40 mA). In certain embodiments, Form IX has an X-ray powder diffraction pattern peak at about 22.7° 2θ using Cu Kα radiation. In certain embodiments, Form IX has X-ray powder diffraction pattern peaks at one, two, three, four, five, six, seven, or more of the X-ray powder diffraction pattern positions provided in FIG. 2A using Cu Kα radiation. In certain embodiments, Form IX has X-ray powder diffraction pattern peaks at one, two, three, four, five, six, seven, eight, nine, or ten of the following approximate positions: about 6.9, about 9.7, about 11.8, about 18.0, about 19.4, about 22.3, about 22.7, about 23.5, about 26.0, and about 29.3°2θ, using Cu Kα radiation.

Form IX can be made by methods as described herein or any method apparent to those of skill in the art. In certain embodiments, Form IX is prepared by stirring Form I and Form VIII of (2-carbamoyl-5-chloro-1H-indol-3-yl)-[3-((E)-2-cyano-vinyl)-5-methyl-phenyl]-(R)-phosphinic acid methyl ester in an organic solvent and harvesting the remaining undissolved residues. In one embodiment, the organic solvent is methanol.

In still anther embodiment, provided herein is Form III, an anhydrous solid form of ((2-carbamoyl-5-chloro-1H-indol-3-yl)-[3-((E)-2-cyano-vinyl)-5-methyl-phenyl]-(R)-phosphinic acid methyl ester. In certain embodiments, Form III has a thermal gravimetric analysis thermogram similar to that provided in FIG. 4B. In certain embodiments, when examined by thermal gravimetric analysis, Form III has a weight loss of no greater than 1% of the total mass when heated from about 25° C. to about 240° C. In certain embodiments, when examined by thermal gravimetric analysis, Form III has a weight loss of between about 0.5% and about 0.9% of the total mass when heated from about 25° C. to about 240° C. In certain embodiments, when examined by thermal gravimetric analysis, Form III has a weight loss of between about 0.7 of the total mass when heated from about 25° C. to about 240° C. In certain embodiments, Form III has a differential scanning calorimetry thermogram similar to that provided in FIG. 4B. In certain embodiments, when examined by differential scanning calorimetry, Form III has one or more of the following thermal events: an endotherm with onset temperature at about 116° C., an endotherm with onset temperature at about 212° C., and an exotherm with an onset temperature at about 165° C. In certain embodiments, Form III has an X-ray powder diffraction pattern similar to that of FIG. 4A using Cu Kα radiation (e.g. 1.5406 angstrom, 40 kV, 40 mA). In certain embodiments, Form III has an X-ray powder diffraction pattern peak at about 20.7° 2θ using Cu Kα radiation. In certain embodiments, Form III has X-ray powder diffraction pattern peaks at one, two, three, four, or more of the X-ray powder diffraction pattern positions provided in FIG. 4A using Cu Kα radiation. In certain embodiments, Form III has X-ray powder diffraction pattern peaks at one, two, three or four of the following positions: about 6.9, about 9.5, about 13.5, and about 20.7° 2θ, using Cu Kα radiation.

Form III of ((2-carbamoyl-5-chloro-1H-indol-3-yl)-[3-((E)-2-cyano-vinyl)-5-methyl-phenyl]-(R)-phosphinic acid methyl ester can be made by methods described herein or any method apparent to those of skill in the art.

In certain embodiments, provided herein is an amorphous form of (2-carbamoyl-5-chloro-1H-indol-3-yl)-[3-((E)-2-cyano-vinyl)-5-methyl-phenyl]-(R)-phosphinic acid methyl ester, or a salt thereof. The amorphous form of (2-carbamoyl-5-chloro-1H-indol-3-yl)-[3-((E)-2-cyano-vinyl)-5-methyl-phenyl]-(R)-phosphinic acid methyl ester can be made by methods as described herein or any method apparent to those of skill in the art.

Certain embodiments provided herein provide mixtures, including physical mixtures and/or solid solutions, of solid forms comprising (2-carbamoyl-5-chloro-1H-indol-3-yl)-[3-((E)-2-cyano-vinyl)-5-methyl-phenyl]-(R)-phosphinic acid methyl ester or a salt thereof.

In certain embodiments, the solid form comprises Form III and amorphous forms.

6.3 Pharmaceutical Compositions

Provided herein are pharmaceutical compositions comprising a solid form provided herein as an active ingredient. In certain embodiments, the pharmaceutical composition comprises at least one release controlling excipient or carrier. In certain embodiments, the pharmaceutical composition comprises at least one nonrelease controlling excipient or carrier. In certain embodiments, the pharmaceutical composition comprises at least one release controlling and at least one nonrelease controlling excipients or carriers.

The active ingredient provided herein may be administered alone, or in combination with one or more other compounds provided herein, one or more other active ingredients. The pharmaceutical compositions that comprise an active ingredient provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., *Drugs and the Pharmaceutical Science*, Marcel Dekker, Inc.: New York, N.Y., 2003; Vol. 126).

In one embodiment, the pharmaceutical compositions are provided in a dosage form for oral administration, which comprise an active ingredient provided herein, and one or more pharmaceutically acceptable diluents, excipients or carriers.

In another embodiment, the pharmaceutical compositions are provided in a dosage form for parenteral administration, which comprises an active ingredient provided herein, and one or more pharmaceutically acceptable diluents, excipients or carriers.

In yet another embodiment, the pharmaceutical compositions are provided in a dosage form for topical administration, which comprises an active ingredient provided herein, and one or more pharmaceutically acceptable diluents, excipients or carriers.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as drotrecogin-α, and hydrocortisone.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

The pharmaceutical compositions provided herein for topical administration may be formulated to be immediate release or modified release, including delayed-, sustained-, pulsed-, controlled-, targeted, and programmed release.

In certain embodiments, a composition is provided comprising the active compound in combination with a polyglycolyzed glyceride known to those of skill in the art. The compound may be incorporated into a semi-solid matrix comprising polyglycolized glycerides, such as GELUCIRE. The polyglycolized glyceride is e.g., a semi-solid excipient composed of fatty acid (C8-C18) esters of glycerol and polyethylene glycol (PEG) esters. In another embodiment, the polyglycolized glyceride GELUCIRE is e.g., a semi-solid excipient composed of fatty acid (C12-C18) esters of glycerol and polyethylene glycol (PEG) esters. The polyglycolized glyceride is optionally a semisolid surfactant.

The polyglycolyzed glyceride includes, e.g., a mixture of mono-, di- and triglycerides and polyethylene glycol (PEG) mono- and diesters, which may be of molecular weight between 200 and 600, where appropriate of free glycerol and free PEG, whose hydrophile-lipophile balance (HLB) value can be adjusted by the length of the PEG chain, and whose melting point can be adjusted by the length of the chains of the fatty acids, of the PEG and by the degree of saturation of the fatty chains, and hence of the starting oil. Examples of such mixtures include GELUCIRE. See, e.g., PCT publication no. WO 2007/038796 and U.S. Pat. Nos. 4,797,286, 5433,951 and 6,171,615, the contents of which are hereby incorporated by reference in their entireties.

6.4 Processes for Preparing the Active Compound

The compounds provided herein can be prepared according to any method apparent to one of skill in the art. Exemplary processes for preparing (2-carbamoyl-5-chloro-1H-indol-3-yl)-[3-((E)-2-cyano-vinyl)-5-methyl-phenyl]-(R)-phosphinic acid methyl ester including isomers and salts thereof are described in U.S. patent application Ser. No. 11/229,150, filed Sep. 16, 2005; PCT US2006/054182, published May 26, 2006; U.S. patent application Ser. No. 11/906,095, filed Sep. 28, 2007; PCT US2007/020900, filed Sep. 28, 2007; and U.S. Prov. Appl. No. 60/932,713, filed May 31, 2007; the disclosures of each of which are incorporated herein by reference in their entirety.

In certain embodiments, the enantiomerically pure compound comprises at least about 80% by weight of the designated enantiomer and at most about 20% by weight of the other enantiomer or other stereoisomer(s), at least about 90% by weight of the designated enantiomer and at most about 10% by weight of the other enantiomer or other stereoisomer(s), at least about 95% by weight of the designated enantiomer and at most about 5% by weight of the other enantiomer or other stereoisomer(s), at least about 96.6% by weight of the designated enantiomer and at most about 3.4% by weight of the other enantiomer or other stereoisomer(s), at least about 97% by weight of the designated enantiomer and at most about 3% by weight of the other enantiomer or other stereoisomer(s), at least about 99% by weight of the designated enantiomer and at most about 1% by weight of the other enantiomer or other stereoisomer(s), or at least about 99.9% by weight of the designated enantiomer and at most about 0.1% by weight of the other enantiomer or other stereoisomer(s). In certain embodiments, the weights are based upon total weight of the compound.

6.5 Methods of Treatment

In one embodiment, provided herein are methods for the treatment or prophylaxis of an HIV infection in a host, comprising administering an antivirally-effective amount of a solid form or pharmaceutical composition described herein. The active ingredient may be combined with a pharmaceutically acceptable carrier, excipient or diluent, and can be administered in combination or alternation with one or more additional therapeutic agents as described herein or known in the art.

The use of an active ingredient described herein in the manufacture of a medicament for the treatment or prophylaxis of an HIV infection in a host, optionally in combination with a pharmaceutically acceptable carrier, excipient or diluent also is provided.

In other embodiments, the host can have been diagnosed by measurement of an anti-HIV antibody titer in blood. In another embodiment, the active ingredient is administered to reduce or prevent symptoms of AIDS (acquired immune deficiency syndrome) in a host. In yet another embodiment, the active ingredients disclosed herein are administered to a host at risk of infection with HIV.

In another embodiment, the active ingredient exhibits activity against drug-resistant forms of HIV, and thus exhibits decreased cross-resistance against currently approved antiviral therapies. The phrase "activity against a drug-resistant form of HIV" means that a compound (or its prodrug or pharmaceutically acceptable salt) is active against the mutant strain with an $EC_{50}$, e.g., of less than approximately 50, 25, 10, or 1 micromolar. In one embodiment, the non-nucleoside reverse transcriptase inhibitor (NNRTI) displays an $EC_{50}$ against a mutant HIV strain of less than approximately 5, 2.5, 1 or 0.1 micromolar. In one non-limiting embodiment, the HIV mutant strain has a reverse transcriptase mutation at lysine 103→asparagine and/or tyrosine 181→cysteine.

Active ingredients provided herein can be assessed for their ability to inhibit reverse transcriptase activity in vitro according to standard screening methods. The spectrum of activity exhibited by any particular compound is determined by evaluating the active ingredient in assays described in this specification or with other confirmatory assays known to those skilled in the art of anti-HIV compounds. Compounds can exhibit an $EC_{50}$ of less than 10-15 µM.

In one embodiment, the efficacy of the active ingredients is measured by the HIV-specific enzyme-linked immunosorbent assay, p24 ELISA. Drug efficacy is expressed as percent inhibition of the HIV p24 antigen in this rapid and sensitive assay. In a related embodiment useful for specific experiments, the efficacy of the active ingredient is determined by a "plaque reduction assay" which measures the concentration of compound necessary to reduce the plaque number of the virus in vitro, according to the methods set forth more particularly herein, by 50% (i.e., the $EC_{50}$ of the compound). In some embodiments the active ingredient exhibits an $EC_{50}$ of less than 15, or less that 10 micromolar to nanomolar amounts in vitro.

6.6 Combination or Alternation Therapy

In certain embodiments, the active ingredient is administered in combination and/or alternation with one or more other anti-HIV agents. In another embodiment, the administration of two or more anti-HIV agents results in a synergistic effect in the inhibition of HIV. In another embodiment, the effect of administering two or more such agents in combination and/or alternation produces an additive effect in inhibiting HIV replication.

In certain embodiments, the active ingredient is administered in combination and/or alternation with one or more anti-HBV or one or more anti-HCV agents. For instance, in certain embodiments, the active ingredient can be administered to a host co-infected with HIV and HBV in combination with an agent effective for the treatment of HBV. The agent effective for the treatment of HBV can be any such agent known to those of skill in the art. Exemplary agents are described herein. In certain embodiments, the active ingredient can be administered to a host co-infected with HIV and HCV in combination with an agent effective for the treatment of HCV. The agent effective for the treatment of HCV can be any such agent known to those of skill in the art.

In combination therapy, effective dosages of two or more agents are administered together, whereas during alternation therapy an effective dosage of each agent is administered serially. The dosages will depend upon absorption, inactivation, and excretion rates of the drugs as well as other factors known to those of skill in the art. Dosage values also will vary with the severity of the condition to be alleviated. For any particular individual, specific dosage regimens and schedules should be adjusted over time to meet the needs of the individual and the professional judgment of the person administering or supervising the administration of the compositions.

Drug resistance most typically occurs by mutation of a gene that encodes for an enzyme used in the viral replication cycle. It has been demonstrated that the efficacy of an anti-HIV drug can be prolonged, augmented or restored by administering the compound in combination or alternation with a second, and perhaps third, antiviral compound that induces a different mutation(s) from that selected for by the principle drug. Such drug combinations simultaneously reduce the possibility of resistance to any single drug and any associated toxic effects. Alternatively, the pharmacokinetics, biodistribution, or other parameters of the drug can be altered by such combination or alternation therapy. For example, the use of a combination of drugs may permit an individual drug within that combination to be given at a dosage lower than what would be required when the drug is administered as a monotherapeutic. Likewise, when drugs that target different stages of the viral life cycle are combined, there exists the possibility for potentiating their effects. Moreover, use of combinations of drugs could lower or eliminate undesirable side-effects from a single drug while still producing anti-viral activity. In general, combination therapy is typically preferred over alternation therapy because it places multiple, simultaneous pressures on the virus.

6.6.1. HCV Agents

Interferons (IFNs) for the treatment of chronic hepatitis have been made available commercially for nearly a decade, and form the basis of currently available approved therapies for HCV. IFNs are glycoproteins produced by immune cells in response to viral infections.

Many patents disclose Flaviviridae, including HCV, treatments that use interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon-alpha for the treatment of infectious diseases including HCV. U.S. Pat. No. 5,849,696 to Chretien et al. discloses the use of thymosins, alone or in combination with interferon, for treating HCV. U.S. Pat. No. 5,830,455 to Valtuena et al. teaches a combination HCV therapy that employs interferon and a free radical scavenger. U.S. Pat. No. 5,738,845 to Imakawa teaches the use of human interferon-tau proteins for treating HCV. Other interferon-based treatments for HCV are given in U.S. Pat. No. 5,676,942 to Testa et al. and U.S. Pat. No. 5,372,808 to Blatt et al. A number of patents also disclose pegylated forms of interferons and their use, such as, for example, U.S. Pat. Nos. 5,747,646; 5,792,834; and 5,834,594 all to Hoffmann-LaRoche, Inc.; PCT WO 99/32139 and WO 99/32140 to Enzon; WO 95/13090 and U.S. Pat. Nos. 5,738,846 and 5,711,944 to Schering Corporation; and U.S. Pat. No. 5,908,621 to Glue et al.

Interferon alpha-2a and interferon alpha-2b currently are approved as monotherapy for the treatment of HCV. ROFERON®-A from Roche is the recombinant form of interferon alpha-2a. PEGASYS® from Roche is the pegylated or polyethylene glycol modified form of interferon alpha-2a. INTRON® A from Schering Corporation is the recombinant form of interferon alpha-2b, and PEG-INTRON® from Schering Corporation is the pegylated form of interferon alpha-2b.

Other forms of interferon alpha as well as interferon beta, gamma, tau and omega currently are in development for the treatment of HCV. Examples included here are INFERGEN, interferon alphacon-1, by InterMune; OMNIFERON, a natural interferon, by Viragen; ALBUFERON by Human Genome Sciences; REBIF, interferon beta-1a, by Ares-Serono; Omega Interferon by BioMedicine; Oral Interferon Alpha by Amarillo Biosciences; and interferons gamma, tau and gamma 1-b by InterMune.

Ribavirin (1-β-D-ribofuranosyl-1-1,2,4-triazolyl-3-carboxamide) is a synthetic, non-interferon inducing, broad spectrum antiviral nucleoside analog sold under the trade name, Virazole (*The Merck Index*, 11*th* Ed., 1989, Editor: Budavari, S., Merck & Co., Inc., Rahway, N.J.; p. 1304). See U.S. Pat. No. 3,798,209 and RE29,835. Structurally ribavirin is similar to guanosine and has in vitro activity against several DNA and RNA viruses including Flaviviridae (Gary L. Davis, 2000, Gastroenterology, 118:S104-S114).

Ribavirin reduces serum amino transferase levels to normal in 40% of patients, but it does not lower serum levels of HCV-RNA (Gary L. Davis, 2000, Gastroenterology, 118: S104-S114). The current standard of care for chronic hepatitis C is combination therapy with an alpha interferon and ribavirin.

Combination therapy with PEG-INTRON® (peginterferon alpha-2b) and REBETOL® (Ribivarin, USP) capsules is available from Schering Corporation. REBETOL® from Schering Corporation also has been approved in combination with INTRON® A (recombinant interferon alpha-2b from Schering Corporation). Roche's PEGASYS® (pegylated interferon alpha-2a) and COPEGUS® (ribavirin) also have been approved for the treatment of HCV infection.

PCTs WO 99/59621, WO 00/37110, WO 01/81359, WO 02/32414 and WO 03/024461 all to Schering Corporation disclose the use of pegylated interferon alpha and ribavirin combination therapy for the treatment of HCV infection. PCTs WO 99/15194, WO 99/64016 and WO 00/24355 all to Hoffmann-LaRoche, Inc., also disclose the combined use of pegylated interferon alpha and ribavirin for HCV infection treatment.

The development of new antiviral agents for treating Flaviviridae infections, especially for infections by hepacivirus HCV, is under development. Specific inhibitors of HCV-derived enzymes like protease, helicase, and polymerase are being studied. Drugs that inhibit steps in HCV replication also are being investigated and include drugs that block production of HCV antigens from RNA (IRES inhibitors), drugs that prevent the normal processing of HCV proteins (glycosylation inhibitors), drugs that block entry of HCV into cells such as by blocking its receptors, and non-specific cytoprotective agents that block cell injury caused by the viral infection. Moreover, molecular approaches to treat infection by hepatitis C virus are being investigated. For example, studies of ribozymes, enzymes that break down specific viral RNA molecules, and antisense oligonucleotides, which are small, complimentary segments of DNA that bind to and inhibit viral RNA, are being studied. A review of HCV treatments can be found in Bymock et al., Antiviral Chemistry & Chemotherapy, 2000, 11:2, and De Francesco et al., Antiviral Res., 2003, 58:1-16.

Other classes of drugs that are being developed to treat Flaviviridae infections and hepatitis C infections in particular include:

1) Protease inhibitors:
   a. Substrate-based NS3 protease inhibitors are disclosed by Attwood et al. in WO 98/22496 and DE 19914474; by Attwood et al. in *Antiviral Chemistry and Chemotherapy*, 1999, 10:259-273; and by Tung et al. in WO 98/17679, which includes alphaketoamides and hydrazinoureas;
   b. Substrate inhibitors that terminate in an electrophile like boronic acid or phosphonate are shown by Llinas-Brunet et al. in WO 99/07734;
   c. Non-substrate based NS3 protease inhibitors such as 2,4,6-trihydroxy-3-nitro-benzamide derivatives, RD3-4082 and RD3-4078 (the former substituted on the amide with a 14-carbon chain and the latter having a para-phenoxyphenyl group), shown by Sudo et al. in *Biochemical and Biophysical Res. Comm.*, 1997, 238: 643-7, and in *Antiviral Chemistry and Chemotherapy*, 1998, 9:186;

d. Sch 68631, a phenanthrenequinone, disclosed by Chu et al. in *Tetrahedron Letters,* 1996, 37:7229-32 and Sch 351633, isolated from the fungus *Penicillium griseofulvum,* disclosed by Chu et al. in *Bioorganic and Medicinal Chem. Lett.,* 9:1949-52;
e. Eglin c, a macromolecule isolated from leech, that exhibits nanomolar potency inhibition against several serine proteases like *S. griseus* proteases A and B, α-chymotrypsin, chymase, and subtilisin, as disclosed by Qasim et al., *Biochemistry,* 1997, 36:1598-1607;
f. Cysteine protease inhibitors for inhibiting HCV endopeptidase 2, as disclosed in U.S. Pat. No. 6,004,933 to Spruce et al.;
g. Synthetic inhibitors of hepatitis C virus NS3 protease or NS4A cofactor that are subsequences of substrates utilized by the protease and/or cofactor, as shown in U.S. Pat. No. 5,990,276 to Zhang et al.;
h. Restriction enzymes to treat HCV as disclosed in U.S. Pat. No. 5,538,865 to Reyes et al.;
i. Peptides such as NS3 serine protease inhibitors of HCV as shown in WO 02/008251 to Corvas International, Inc., and in WO 02/08187 and WO 02/008256 to Schering Corporation;
j. HCV tripeptide inhibitors, as disclosed in U.S. Pat. Nos. 6,534,523; 6,410,531; and 6,420,380 to Boehringer Ingelheim and WO 02/060926 to Bristol Myers Squibb;
k. Diaryl peptides like serine protease inhibitors of HCV as taught by Schering Corporation in WO 02/48172;
l. Imidazolidinones like NS3 serine protease inhibitors of HCV as disclosed in WO 02/08198 to Schering Corporation and WO 02/48157 to Bristol Myers Squibb; and
m. HCV protease inhibitors as taught by Vertex Pharmaceuticals in WO 98/17679 and by Bristol Myers Squibb in WO 02/48116.

2) Thiazolidine derivatives that show relevant inhibition in a reverse-phase HPLC assay with an NS3/4A fusion protein and NS5A/5B substrate, as demonstrated by Sudo et al., *Antiviral Res.,* 1996, 32:9-18, especially compounds RD4 6205, RD4 6193, and RD-1-6250 that have a fused cinnamoyl moiety substituted by a long alkyl chain;
3) Thiazolidines and benzanilides as disclosed by Kakiuchi et al., J. *EBS Letters,* 421:217-220, and Takeshita et al., *Analytical Biochemistry,* 1997, 247:242-46;
4) Helicase inhibitors as disclosed by Diana et al. in U.S. Pat. No. 5,633,358 and WO 97/36554;
5) Nucleotide polymerase inhibitors and gliotoxin as shown by R. Ferrari et al., *J. Virology,* 1999, 73:1649-54;
6) Cerulenin, a natural product shown by V. Lohmann et al., *Virology,* 1998, 249:108-118;
7) Antisense phosphorothioate oligodeoxynucleotides (S-ODN) complementary to sequence stretches in the 5'non-coding (NCR) of the Flaviviridae virus s demonstrated by M. Alt et al., *Hepatology,* 1995, 22:707-717;
8) Nucleotides 326-348 comprising the 3' end of the NCR and nucleotides 371-388 located in the core coding region of the HCV RNA, as shown by M. Alt et al., *Archives of Virology,* 1997, 142:589-599; Galderisi et al., *J. of Cellular Physiology,* 1999, 181:251-257;
9) Inhibitors of IRES-dependent translation as disclosed by Ikeda et al., JP-08268890, and Y. Kai et al., JP-10101591
10) Ribozymes, such as nuclease-resistant ribozymes as shown by D. D. Maccjak et al., *Hepatology,* 1999, 30: abstract no. 995; Barber et al. in U.S. Pat. No. 6,043,077; and Draper et al. in U.S. Pat. Nos. 5,869,253 and 5,610, 054;
11) Nucleoside analogs including the use of branched nucleosides in the treatment of flaviviruses, pestiviruses, and hepaciviruses, as shown by Idenix Pharmaceuticals in WO 01/92282, WO 01/90121, U.S. Pat. No. 6,812,219, and U.S. Pat. No. 6,914,054, where a method is disclosed for the treatment of hepatitis C, pestivirus and/or flavivirus infection in humans and other host animals that includes administering an effective amount of biologically active 1', 2', 3' or 4'-branched β-D or β-L nucleosides or a pharmaceutically acceptable salt or derivative thereof, administered either alone or in combination with another antiviral agent, optionally in a pharmaceutically acceptable carrier. Nucleoside analogues are also found in WO 01/32153 and WO 01/60315 to BioChem Pharma, Inc. (now Shire Biochem, Inc.); WO 02/057425 and WO 02/057287 filed by Merck & Co., Inc.; WO 02/18404 by Roche; WO 01/79246, WO 02/32920, and WO 02/48165 from Pharmasset, Ltd.; and WO 99/43691 to Emory University. At the Oral Session V, Hepatitis C Virus, Flaviviridae, 16th International Conference on Antiviral Research, Apr. 27, 2003, Savannah, Ga., 2'-modified nucleosides for inhibition of HCV were described by Eldrup et al.; nucleoside analogues as possible inhibitors of HCV RNA replication were taught by Bhar et al. (p. A75), wherein the author reported that 2'-modified nucleosides demonstrate potent inhibitory activity in cell-based replicon assays; the effect of 2'-modified nucleosides on HCV RNA replication was reported by Olsen et al. (p. A76).

12) Miscellaneous compounds being developed to treat Flaviviridae infections and hepatitis C infections in particular include: 1-amino-alkylcyclohexanes as described in U.S. Pat. No. 6,034,134 to Gold et al.; alkyl lipids, vitamin E and other antioxidants in U.S. Pat. No. 5,922,757 to Chojkier et al.; squalene, amantadine, and bile acids as shown in U.S. Pat. No. 5,846,964 to Ozeki et al.; N-(phosphonoacetyl)-L-aspartic acid and piperidines as found in U.S. Pat. No. 5,830,905 Diana et al.; benzenedicarboxamides as disclosed in U.S. Pat. No. 5,633,388 to Diana et al.; polyadenylic acid derivatives as described in U.S. Pat. No. 5,496, 546 to Wang et al.; 2',3'-dideoxyinosine as found in U.S. Pat. No. 5,026,687 to Yarchaon et al.; benzimidazoles as demonstrated in U.S. Pat. No. 5,891,874 to Colacino et al.; and plant extracts as shown in U.S. Pat. No. 5,837,257 to Tsai et al. and U.S. Pat. No. 5,725,859 to Omer et al.

13) Compounds for treatment of hepatitis C virus, including: Interleukin-10 by Schering Plough; IP-501 by Interneuron; Merimebodib (VX-497) by Vertex; AMANTADINE® (Symmetrel) by Endo Labs Solvay; HEPTAZYME® by RPI; IDN-6556 by Idun Pharmaceuticals; XTL-002 by XTL; HCV/MF59 by Chiron; CIVACIR® (Hepatitis C Immune Globulin) by NABI; LEVOVIRIN® by ICN/Ribapharm; VIRAMIDINE® by ICN/Ribapharm (Valeant); ZADAXIN® (thymosin alpha-1) by Sci Clone; thymosin plus pegylated interferon by Sci Clone; CEPLENE® (histamine dihydrochloride) by Maxim; VX 950/LY 570310 by Vertex/Eli Lilly; ISIS 14803 by Isis Pharmaceutical/ Elan; JTK 003 by AKROS Pharma; BILN-2061 by Boehringer Ingelheim; CellCept (mycophenolate mofetil) by Roche; T67 (β-tubulin inhibitor) by Tularik; a therapeutic vaccine directed to E2 by Innogenetics; FK788 by Fujisawa Healthcare, Inc.; IdB 1016 (Siliphos, oral silybin-phosphatydylcholine phytosome); an RNA replication inhibitor VP50406 by ViroPharma/Wyeth; therapeutic vaccines by Intercell and Epimmune/Genencor; an IRES inhibitor by Anadys; ANA 245 and ANA 246 by Anadys; immunotherapy "Therapore" by Avant; protease inhibitors by Bristol Myers Squibb/Axys and Corvas/Schering; a helicase inhibitor by Vertex; a fusion inhibitor by Trimeris; T cell therapy by CellExSys; polymerase inhibitor by Biocryst; targeted RNA chemistry by PTC Therapeutics; Dication by Immtech, International; protease inhibitors by Agouron and Chiron/Medivir; antisense therapies by AVI BioPharma and Hybridon; a hemopurifier by Aethlon Medical; a therapeutic vaccine by Merix; "Chron-VacC", a therapeutic vaccine, by Tripep; UT 231B by United Therapeutics; protease, helicase and polymerase inhibitors by Genelabs Technologies; IRES inhibitors by Immusol; R803 by Rigel Pharmaceuticals; INFERGEN® (interferon alphacon-1) by InterMune; OMNIFERON® (natural interferon) by Viragen; ALBUFERON® by Human Genome Sciences; REBIF® (interferon beta-1a) by Ares-Serono; Omega Interferon by BioMedicine; Oral Interferon Alpha by Amarillo Biosciences; interferons gamma, tau and gamma-1b by InterMune; consensus interferon by Valeant; Nexavar by Onyx Pharmaceuticals; PI-88 by Progen Industries; doxorubicin transdrug by BioAlliance Pharma; JBK-122 by Jenken Biosciences; Valopicitabine by Idenix; VGX-410C by VGX Pharmaceuticals; Celgosivir by Migenix; Suvus by Bioenvision; Multiferon by Viragen; omega interferon by Intarcia; INNO0101 (E1) by Innogenetics; PF-03491390 by Pfizer; medusa interferon by Flamel Technologies; IC41 by Intercell; SCH 503034 by Schering; G126270 by GlaxoSmithKline; GV1001 by Pharmexa; R1626 by Roche; Maxygen/Roche; R7128 by Pharmasset/Roche; Belerofon by Nautilus Biotech; Alinia by Romark; Bavituximab by Peregrine; Oral Interferon alpha by Amarillo Biosciences; NOV-205 by Novelos; CGI 5005 by GlobeImmune; HCV-796 by ViroPharma/Wyeth; HCV/MF59 by Chiron/Norvartis; EMZ702 by Transition Therapeutics; AVI-4065 by Biopharma; ANA975 by ANADYS; MitoQ by Antipodean Pharmaceuticals, Inc; ACH-0137171 by Achillion Pharmaceuticals; R1626 by Roche; XTL-2125 by XTL; XTL-6865 by XTL; BLX-883 by Biolex Therapeutics/OctoPlus; DEBIO-025 by DEBIO; and UT-231B by United Therapeutics; and 14) Nucleoside prodrugs as previously described for the treatment of other forms of hepatitis, including 2'-deoxy-β-L-nucleosides and their 3'-prodrugs for the treatment of HBV as disclosed in WO 00/09531 and WO 01/96353 to Idenix Pharmaceuticals; and therapeutic esters of acyclovir as shown in U.S. Pat. No. 4,957,924 to Beauchamp.

Other examples of antiviral agents that can be used in combination and/or alternation with the compounds disclosed herein include, but are not limited to, agents such as VX-950 and interferon. Interferons that may be used include Schering-Plough's alpha interferon-2b products, Intron® A and PEG-Intron™; and Hoffman La Roche's Co-Pegasus and PEGASYS (pegylated interferon alfa-2a).

6.6.2. Hepatitis B Agents

The hepatitis B agent can be any agent known to those of skill in the art to be effective for the treatment of hepatitis B infection in a host in need thereof. In certain embodiments, the hepatitis B agent is interferon-alpha (Intron A, Schering-Plough), pegylated interferon (Pegasus, Roche), lamivudine (Epivir-HBV, Zeffix, or Heptodin, Glaxo-Smithkline), adefovir dipivoxil (Hepsera, Gilead), entecavir (Baraclude, Bristol-Myers-Squibb), telbivudine (Tyzeka or Sebivo, Idenix) or HBV immuneglobulin (HyperHEP S/D, Talecris; Nabi-HBV, Nabi; Hepa Gam B, Cangene).

In certain embodiments, the hepatitis B agent is FTC (Emtricitabine, Gilead), L-FMAU (Clevudine, Pharmasset; Levovir, Bukwang), tenofovir (Viread, Gilead), monoval LdC (Valtorcitabine, Idenix), DAPD (Amdoxovir, RFS Pharm LLC), Ana 380 (LB80380, Anadys), remofovir (Pradefovir, Schering-Plough), racivir (RCV, Pharmasset), BAM-205 (NOV-205, Novelos), XTL-001 (HepeX-B, XTL Biopharm, Cubist), nitoxanide (Alinia, Romark Labs), UT 231-B (United Therapeutics), Bay 41-4109 (Bayer), EHT899 (Enzo Biochem), thymosin alpha-1 (Zadaxin, SciClone), Hi-8 HBV (Oxxon), eiRNA (HepX, Nucleonics), HepaVaxx B (Virexx), HBV Core Antigen Vaccine (Emergent Europe), or SpecifEx-HepB (Chromos).

6.6.3. Other Antiviral Agents Including Anti-HIV Agents

Any of the viral treatments known in the art or described herein can be used in combination or alternation with the active ingredients described herein. Non-limiting examples include a) protease inhibitors; b) thiazolidine derivatives; c) helicase inhibitors; d) benzanilides; e) phenanthrenequinones; f) polymerase inhibitors and gliotoxin; g) antisense phosphorothioate oligodeoxynucleotides (S-ODN); h) inhibitors of IRES-dependent translation; i) ribozymes; j) nucleoside analogues; k) disubstituted nucleoside analogues as disclosed by Idenix Pharmaceuticals in WO 01/90121, WO 01/92282, WO 04/00300, WO 04/002999, and WO 04/002422; 1) 2'-fluoronucleoside analogues; m) 1-$NH_2$-alkylcyclohexanes; n) alkyl lipids; o) vitamin E and other antioxidants; p) squalene, amantadine and bile acids; q) N-(phosphonoacetyl)-L-aspartic acid; r) benzenedicarboxamides; s) polyadenylic acid derivatives; t) benzimidazoles; u) 2',3'-dideoxyinosine; v) plant extracts; w) piperidines; and x) other compounds currently in preclinical or clinical development for the treatment of pestiviruses, flaviviruses and/or hepacivirus, including ribavirin and the families of interferons.

The second antiviral agent for the treatment of HIV can be, for example, a protease inhibitor, an HIV-integrase inhibitor, a chemokine inhibitor, or a reverse transcriptase inhibitor ("RTI"), the latter of which can either be a synthetic nucleoside reverse transcriptase inhibitor ("NRTI") or a non-nucleoside reverse transcriptase inhibitor ("NNRTI"). In other embodiments, a second or third compound may be a pyrophosphate analog or a fusion-binding inhibitor. A list compiling resistance data collected in vitro and in vivo for certain antiviral compounds is found in Schinazi et al., Mutations in retroviral genes associated with drug resistance, International Antiviral News, 1997, 5(8).

In certain embodiments, the active ingredient is administered in combination and/or alternation with FTC (2',3'-dideoxy-3'-thia-5-fluorocytidine); 141W94 (amprenavir, Glaxo Wellcome, Inc.); Viramune (nevirapine); Rescriptor (delavirdine); DMP-266 (efavirenz); DDI (2',3'-dideoxyinosine); 3TC (3'-thia-2',3'-dideoxycytidine); DDC (2',3'-dideoxycytidine), abacavir (1592U89), which is (1S,4R)-4-[(2-amino-6-cyclopropyl-amino)-9H-purin-9-yl]-2-cyclopentene-1-methanol succinate, Tenofovir DF (Viread), D4T, or AZT.

Other examples of antiviral agents that can be used in combination and/or alternation with the compounds disclosed herein include, but are not limited to, foscarnet; carbovir; acyclovir; interferon; fusion inhibitors such as enfuvirtide; and β-D-dioxolane nucleosides such as β-D-dioxolanylguanine (DXG), β-D-dioxolanyl-2,6-diaminopurine (DAPD), and β-D-dioxolanyl-6-chloropurine (ACP). Interferons that may be used include Schering-Plough's alpha interferon-2b products, Intron® A and PEG-Intron™; and Hoffman La Roche's Co-Pegasus and PEGASYS (pegylated interferon alfa-2a). Combinations with which the 3-phosphoindoles can be administered include Epzicom (ABC+3TC), Trizivir (ABC+3TC+AZT), Truvada® (Emtriva® (emtricitabine; FTC) and Viread® (tenofovir disoproxil fumarate; tenofovir DF)) and Combivir (AZT+3TC).

Examples of protease inhibitors that can be used in combination and/or alternation with the compounds disclosed herein include, but are not limited to indinavir ({1(1S,2R),5 (S)}-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythro-pentoamide sulfate; Merck & Co., Inc.); nelfinavir (Agouron); ritonavir (Abbott Labs), saquinavir (Roche); Amprenavir; Atazanavir; Fosamprenavir; Kaletra; and DMP-450 {[4R-4(r-a,5-a,6-b,7-6)-hexahydro-5,6-bis(hydroxy)-1, 3-bis(3-amino)-phenyl]methyl-4,7-bis(phenylmethyl)-2H-1,3-diazepin-2-one}-bismesylate (Triangle Pharmaceuticals, Inc.).

Other compounds that can be administered in combination or alternation with the active ingredient to augment its antiviral properties include (1S,4R)-4-[2-amino-6-cyclopropyl-amino-9H-purin-9-yl]-2-cyclopentene-1-methanol succinate (1592U89, a carbovir analog, from GlaxoSmithKline); BILA 1906 (N-{1S-[[[3-[2S-{(1,1-dimethylethyl)amino]carbonyl}-4R-]3-pyrindinylmethyl)thio]-1-piperidinyl]-2R-hydroxy-1S-phenylmethyl)propyl]-amino]carbonyl]-2-methylpropyl}-2-quinolinecarboxamide) (Bio Mega/Boehringer Ingelheim); BILA 2185 (N-(1,1-dimethylethyl)-1-[2S-[[[2-2,6-dimethyl-phenoxy]-1-oxoethyl]amino]-2R-hydroxy-4-phenylbutyl]4R-pyridinylthio-2-piperidine-carboxamide) (Bio Mega/Boehringer Ingelheim); BM+51.0836 (triazolo-iso-indolinone derivative) and BMS 186,318 (aminodiol derivative HIV-1 protease inhibitor) (Bristol-Myers Squibb); d4API (9-[2,5-dihydro-5-(phosphonomethoxy)-2-furanyl]-adenine) (Gilead); HBY097 (S-4-isopropoxycarbonyl-6-methoxy-3-[methylthio-methyl]-3,4-dihydroquinoxalin-2 (1H)-thione); HEPT (1-[(2-hydroxy-ethoxy)methyl]6-[phenylthio]-thymine); KNI-272 ((2S,3S)-3-amino-2-hydroxy-4-phenylbutyric acid-containing tripeptide); L-697, 593 (5-ethyl-6-methyl-3-(2-phthalimido-ethyl)pyridin-2 (1H)-one); L-732,524 (hydroxy-aminopentane amide HIV-1, protease inhibitor) (Merck & Co.); L-697,661 (3-{[(-4,7-dichloro-1,3-benzoxazol-2-yl)methyl]amino}-5-ethyl-6-methyl-pyridin-2(1H)-one); L-FDDC ((−)-β-L-5-fluoro-2', 3'-dideoxycytidine); L-FDOC ((−)-β-L-5-fluoro-dioxolane cytosine); PFA (phosphonoformate; "foscarnet"; Astra); PMEA (9-(2-phosphonylmethoxyethyl)adenine) (Gilead); PMPA ((R)-9-(2-phosphonylmethoxy-propyl)-adenine) (Gilead); Ro 31-8959 (hydroxyethylamine derivative HIV-1 protease inhibitor) (Roche); RPI-3121 (peptidyl protease inhibitor, 1-[(3S)-3-(n-alpha-benzyloxy-carbonyl)-1-as-parginyl)-amino-2-hydroxy-4-phenylbutyryl]-n-tert-butyl-1-proline amide); 2720 (6-chloro-3,3-dimethyl-4-(isopropenyloxycarbonyl)-3,4-dihydro-quinoxalin-2(1H)thione); SC-52151 (hydroxyethylurea isostere protease inhibitor) (G.D. Searle); SC-55389A (hydroxyethyl-urea isostere protease inhibitor (G.D. Searle); TIBO R82150 ((+)-(5S)-4,5,6, 7-tetrahydro-5-methyl-6-(3-methyl-2-butenyl)-imidazo-[4, 5,1-jk]-[1,4]-benzodiazepin-2(1H)-thione) (Janssen Pharmaceuticals); TIBO 82913 ((+)-(5S)-4,5,6,7-tetrahydro-9-chloro-5-methyl-6-(3-methyl-2-butenyl)imidazo[4,5,1-jk]-[1,4]-benzo-diazepin-2(1H)-thione (Janssen Pharmaceuticals); TSAO-m3T ([2',5'-bis-O-(tert-butyldimethylsilyl)-3'-spiro-5'-(4'-amino-1',2'-oxathiole-2',2'-dioxide)]-β-D-pentofuranosyl-N3-methyl-thymine); U90152 (1-[3-[(1-methylethyl-amino]2-pyridinyl]-4-[[5-[(methylsulphonyl)-amino]-1H-indol-2-yl]-carbonyl]-piperazine); UC (thiocarboxanilide derivatives) (Uniroyal); UC-781 (N-[4-chloro-3-(3-methyl-2-butenyloxy)phenyl]-2-methyl-3-furancarbothioamide); UC-82 (N-[4-chloro-3-(3-methyl-2-butenyloxy)phenyl]-2-methyl-3-thiophenecarbothioamide); VB 11,328 (hydroxyethyl-sulphonamide protease inhibitor) (Vertex/Glaxo Wellcome); XM 323 (cyclic urea protease inhibitor) (Dupont Merck); and penciclovir. In yet another embodiment, the compound provided herein is administered in combination with the protease inhibitor LG 1350.

The following drugs can be used in combination and/or alternation with the compounds provided herein.

| Drug Name | Manufacturer |
|---|---|
| 3TC, Epivir ® brand lamivudine | GlaxoSmithKline |
| abacavir generic Ziagen ®, ABC, or 1592U89 | GlaxoSmithKline |
| ABC, Ziagen ® brand abacavir, or 1592U89 | GlaxoSmithKline |
| ABT-378/r, or Kaletra ® brand lopinavir/ritonavir | Abbott Laboratories |
| AG-1549, S-1153, or capravirine (CPV) | Pfizer |
| AG1661, Remune ® brand HIV-1 Immunogen, or Salk vaccine | Immune Response Corp. |
| Agenerase ® brand amprenavir (APV), 141W94, or VX-478 | GlaxoSmithKline |
| aldesleukin generic Proleukin ®, or Interleukin-2 (IL-2) | Chiron Corporation |
| amdoxovir, or DAPD | Gilead Sciences |
| amprenavir generic Agenerase ®, APV, 141W94, or VX-478 | GlaxoSmithKline |
| Aptivus ® | Boehringer Ingelheim |
| APV, Agenerase ® brand amprenavir, 141W94, or VX-478 | GlaxoSmithKline |
| atazanavir generic Reyataz ™, or BMS-232632 | Bristol-Myers Squibb |
| Atripla ® | Bristol-Myers Squibb and Gilead |
| AZT, Retrovir ® brand zidovudine (ZDV) | GlaxoSmithKline |
| Bis(POC) PMPA, Viread ® brand tenofovir DF | Gilead Sciences |
| BMS-232632, or Reyataz ™ brand atazanavir | Bristol-Myers Squibb |
| BMS-56190, or DPC-083 | Bristol-Myers Squibb |
| calanolide A | Sarawak Medichem |
| capravirine (CPV), AG-1549, or S-1153 | Pfizer |
| Combivir ® brand zidovudine + lamivudine, or AZT + 3TC | GlaxoSmithKline |
| CPV (capravirine), AG-1549, or S-1153 | Pfizer |
| Crixivan ® brand indinavir (IDV), or MK-639 | Merck & Co. |
| d4T, Zerit ® brand stavudine, or BMY-27857 | Bristol-Myers Squibb |
| DAPD, or amdoxovir | Gilead Sciences |
| ddC, or Hivid ® brand zalcitabine | Hoffmann-La Roche |
| ddI, Videx ® brand didanosine, or BMY-40900 | Bristol-Myers Squibb |
| delavirdine generic Rescriptor ®, DLV, or U-90152S/T | Pfizer |
| didanosine generic Videx ®, ddI, or BMY-40900 | Bristol-Myers Squibb |

-continued

| Drug Name | Manufacturer |
|---|---|
| DLV, Rescriptor ® brand delavirdine, or U-90152S/T | Pfizer |
| DPC-083, or BMS-56190 | Bristol-Myers Squibb |
| Droxia ® brand hydroxyurea (HU) | Bristol-Myers Squibb |
| efavirenz generic Sustiva ®, or EFV | Bristol-Myers Squibb |
| EFV, Sustiva ® brand efavirenz | Bristol-Myers Squibb |
| emtricitabine generic Emtriva ™, or FTC | Gilead Sciences |
| Emtriva ® brand emtricitabine, or FTC | Gilead Sciences |
| enfuvirtide generic Fuzeon ™, or T-20 | Trimeris and Hoffmann-La Roche |
| Epivir ® brand lamivudine, or 3TC | GlaxoSmithKline |
| epoetin alfa (erythropoietin) generic Procrit ® | Ortho Biotech |
| Epzicom ® | GlaxoSmithKline |
| erythropoietin (epoetin alfa) generic Procrit ® | Ortho Biotech |
| Fortovase ® brand saquinavir (Soft Gel Cap), or SQV (SGC) | Hoffmann-La Roche |
| fosamprenavir, or GW-433908, or VX-175 | GlaxoSmithKline |
| FTC, or Emtriva ® brand emtricitabine | Gilead Sciences |
| Fuzeon ™ brand enfuvirtide, or T-20 | Trimeris and Hoffmann-La Roche |
| GW-433908, or fosamprenavir, or VX-175 | GlaxoSmithKline |
| HE2000, or alpha-epibromide | HollisEden Pharmaceuticals |
| HIV-1 Immunogen generic Remune ®, Salk vaccine, or AG1661 | Immune Response Corp. |
| Hivid ® brand zalcitabine, or ddC | Hoffmann-La Roche |
| HU, or Droxia ® brand hydroxyurea | Bristol-Myers Squibb |
| hydroxyurea generic Droxia ®, or HU | Bristol-Myers Squibb |
| IDV, Crixivan ® brand indinavir, or MK-639 | Merck & Co. |
| IL-2 (Interleukin-2), or Proleukin ® brand aldesleukin | Chiron Corporation |
| indinavir generic Crixivan ®, IDV, or MK-639 | Merck & Co. |
| Interleukin-2 (IL-2), or Proleukin ® brand aldesleukin | Chiron Corporation |
| Isentress brand raltegravir | Merck |
| Invirase ® brand saquinavir (Hard Gel Cap), SQV (HGC), or Ro-31-8959 | Hoffmann-La Roche |
| Kaletra ® brand lopinavir/ritonavir, or ABT-378/r | Abbott Laboratories |
| lamivudine generic Epivir ®, or 3TC | GlaxoSmithKline |
| Lexiva ® | GlaxoSmithKline |
| lopinavir/ritonavir generic Kaletra ®, or ABT-378/r | Abbott Laboratories |
| MK-639, Crixivan ® brand indinavir (IDV) | Merck & Co. |
| nelfinavir generic Viracept ®, NFV, or AG-1343 | Pfizer |
| nevirapine generic Viramune ®, NVP, or BI-RG-587 | Boehringer Ingelheim |
| NFV, Viracept ® brand nelfinavir, or AG-1343 | Pfizer |
| Norvir ® brand ritonavir (RTV), or ABT-538 | Abbott Laboratories |
| NVP, Viramune ® brand nevirapine, or BI-RG-587 | Boehringer Ingelheim |
| PNU-140690, or tipranavir | Boehringer Ingelheim |
| Prezista ® | Tibotec |
| PRO-542 | Progenics Pharmaceuticals |
| Procrit ® brand epoetin alfa (erythropoietin) | Ortho Biotech |
| Proleukin ® brand aldesleukin, or Interleukin-2 (IL-2) | Chiron Corporation |
| Remune ® brand HIV-1 Immunogen, or Salk vaccine | Immune Response Corp. |
| Rescriptor ® brand delavirdine (DLV), or U-90152S/T | Pfizer |
| Retrovir ® brand zidovudine (ZDV), or AZT | GlaxoSmithKline |
| Reyataz ™ brand atazanavir, or BMS-232632 | Bristol-Myers Squibb |
| ritonavir generic Norvir ®, RTV, or ABT-538 | Abbott Laboratories |
| RTV, Norvir ® brand ritonavir, or ABT-538 | Abbott Laboratories |
| Salk vaccine, Remune ® brand HIV-1 Immunogen, or AG1661 | Immune Response Corp. |
| saquinavir (Hard Gel Cap) generic Invirase ®, SQV (HGC), or Ro-31-8959 | Hoffmann-La Roche |
| saquinavir (Soft Gel Cap) generic Fortovase ®, or SQV (SGC) | Hoffmann-La Roche |
| SCH-C | Schering-Plough |
| Selzentry brand maraviroc | Pfizer |
| Serostim ® brand somatropin | Serono Laboratories |
| somatropin generic Serostim ® | Serono Laboratories |
| SQV (HGC), Invirase ® brand saquinavir (Hard Gel Cap), or Ro-31-8959 | Hoffmann-La Roche |
| SQV (SGC), or Fortovase ® brand saquinavir (Soft Gel Cap) | Hoffmann-La Roche |
| stavudine generic Zerit ®, d4T, or BMY-27857 | Bristol-Myers Squibb |
| Sustiva ® brand efavirenz (EFV) | Bristol-Myers Squibb |
| T-1249 | Trimeris and Hoffmann-La Roche |
| T-20, or Fuzeon ™ brand enfuvirtide | Trimeris and Hoffmann-La Roche |
| TDF, tenofovir DF generic Viread ™, or Bis(POC) PMPA | Gilead Sciences |
| tenofovir DF (TDF) generic Viread ®, Bis(POC) PMPA | Gilead Sciences |
| tipranavir, or PNU-140690 | Boehringer Ingelheim |
| TMC-114 | Tibotec-Virco Group |
| TMC-125 | Tibotec-Virco Group |
| Trizivir ® brand abacavir + zidovudine + lamivudine (ABC + AZT + 3TC) | GlaxoSmithKline |
| Truvada ® | Gilead |

-continued

| Drug Name | Manufacturer |
|---|---|
| Videx ® brand didanosine, ddI, or BMY-40900 | Bristol-Myers Squibb |
| Videx ® EC brand didanosine (ddI): delayed-release capsules | Bristol-Myers Squibb |
| Viracept ® brand nelfinavir (NFV), or AG-1343 | Pfizer |
| Viramune ® brand nevirapine (NVP), or BI-RG-587 | Boehringer Ingelheim |
| Viread ® brand tenofovir DF, or Bis(POC) PMPA | Gilead Sciences |
| VX-175, or fosamprenavir, or GW-433908 | GlaxoSmithKline |
| zalcitabine generic Hivid ®, or ddC | Hoffmann-La Roche |
| ZDV, Retrovir ® brand zidovudine, or AZT | GlaxoSmithKline |
| Zerit ® brand stavudine, d4T, or BMY-27857 | Bristol-Myers Squibb |
| Ziagen ® brand abacavir (ABC), or 1592U89 | GlaxoSmithKline |
| zidovudine generic Retrovir ®, AZT, or ZDV | GlaxoSmithKline |

Additional drugs that can be used in combination and/or alternation with the active ingredients include:

| | | |
|---|---|---|
| GW5634 (GSK) | MIV-150 (Medivir/Chiron) | Tipranavir (B-I) |
| RO033-4649 (Roche) | TMC125 (Tibotec) | TNX-355 (Tanox) |
| GW640385 (GSK/Vertex) | TMC114 (Tibotec) | UK-427,857 (Pfizer) |
| Elvucitabine (Achillion Ph.) | Alovudine (FLT) (B-I) | TAK-220 (Takeda) |
| MIV-210 (GSK/Medivir) | Racivir (Pharmasset) | PRO 542 (Progenics Pharm) |
| SPD754 (Shire Pharm.) | Reverset (Incyte Corp.) | Schering C/D (417690) |
| FP21399 (Fuji Pharm.) | AMD070 (AnorMed) | |
| GW873140 (GSK) | BMS-488043 (BMS) | |

The following drugs can be used in combination and/or alternation with the active ingredients provided herein.

| Brand Name | Generic Name | Use | Manufacturer Name |
|---|---|---|---|
| Abelcet, Ambisome | Amphotericin B, ABLC | antifungal for aspergillosis | various |
| Bactrim, Septra | sulfamethoxazole and trimethoprim | antiprotozoal antibiotic for *Pneumocystis carinii* pneumonia treatment and prevention | various |
| Biaxin, Klacid | Clarithromycin | antibiotic for *Mycobacterium avium* prevention and treatment | Abbott Laboratories |
| Cytovene | ganciclovir, DHPG | antiviral for CMV retinitis | Roche |
| DaunoXome | daunorubicin-liposomal | chemotherapy for Kaposi's sarcoma | Gilead |
| Diflucan | Fluconazole | antifungal for candidiasis, cryptococcal meningitis | Pfizer |
| Doxil | doxorubicin hydrochloride-liposomal | chemotherapy for Kaposi's sarcoma | Ortho Biotech |
| Famvir | Famciclovir | antiviral for herpes | Novartis |
| Foscarnet | Foscavir | antiviral for herpes, CMV retinitis | Astra Pharmaceuticals |
| Gamimune N | immune globulin, gamma globulin, IGIV | immune booster to prevent bacterial infections in children | Bayer Biologicals |
| Intron A | interferon alfa-2b | Karposi's sarcoma, hepatitis C | Schering |
| Marinol | Dronabinol | treat appetite loss | Roxane Laboratories |
| Megace | megestrol acetate | treat appetite, weight loss | Bristol Myers-Squibb |
| Mepron | Atovaquone | antiprotozoal antibiotic for *Pneumocystis carinii* pneumonia treatment and prevention | GlaxoSmithKline |
| Mycobutin, Ansamycin | Rifabutin | antimycobacterial antibiotic for *Mycobacterium avium* prevention | Adria Pharmaceuticals |
| NebuPent | Pentamidine | antiprotozoal antibiotic for *Pneumocystis carinii* pneumonia prevention | Fujisawa |
| Neutrexin | trimetrexate glucuronate and leucovorin | antiprotozoal antibiotic for *Pneumocystis carinii* pneumonia treatment | MedImmune |
| Panretin gel | alitretinoin gel 0.1% | AIDS-related Karposi's sarcoma | Ligand Pharmaceuticals |
| Procrit, Epogen | erythropoetin, EPO | treat anemia related to AZT therapy | Amgen |

| Brand Name | Generic Name | Use | Manufacturer Name |
|---|---|---|---|
| Roferon A | interferon alfa-2a | Karposi's sarcoma and hepatitis C | Roche |
| Serostim | somatropin rDNA | treat weight loss | Serono |
| Sporanox | Itraconazole | antifungal for blastomycosis, histoplasmosis, aspergillosis, and candidiasis | Janssen Pharmaceuticals |
| Taxol | Paclitaxel | Karposi's sarcoma | Bristol Myers-Squibb |
| Valcyte | Valganciclovir | antiviral for CMV retinitis | Roche |
| Vistide | cidofovir, HPMPC | antiviral for CMV retinitis | Gilead |
| Vitrasert implant | ganciclovir insert | antiviral for CMV retinitis | Bausch & Lomb |
| Vitravene intravitreal injectable | fomivirsen sodium injection | antiviral for CMV retinitis | Isis Pharmaceuticals |
| Zithromax | Azithromycin | antibiotic for *Mycobacterium avium* | Pfizer |

Products that have been allowed to proceed as Investigational New Drugs (IND) by the FDA for the treatment of complications of HIV infection and AIDS can be used. The following drugs can be used in combination and/or alternation with the active ingredients provided herein.

Trimetrexate glucuronate for the treatment of *Pneumocystis carinii* pneumonia in AIDS patients who cannot tolerate standard forms of treatment.

Ganciclovir for the treatment of cytomegalovirus retinitis in AIDS patients.

Aerosolized pentamidine for the prevention of *Pneumocystis carinii* pneumonia in AIDS patients.

Erythropoietin for the treatment of zidovudine-related anemia.

Atovaquone for the treatment of AIDS patients with *Pneumocystis carinii* pneumonia who are intolerant or unresponsive to trimethoprim-sulfamethoxazole.

Rifabutin for prophylaxis against *Mycobacterium avium* complex bacteremia in AIDS patients.

Vistide intravenous cidofovir for HIV-infected persons with relapsing cytomegalovirus (CMV) retinitis that has progressed despite treatment (Hoffmann-La Roche).

Serostim, a mammalian derived recombinant human growth hormone, for the treatment of AIDS-related wasting (Serono Laboratories).

In particular embodiments, the active ingredients disclosed herein can be administered in combination or alternation with one, two or more other anti-HIV agents. In one subembodiment, the additional agent is selected from:
15) a protease inhibitor optionally selected from amprenavir, tipranavir, indinavir, saquinavir (including saquinavir mesylate), lopinavir, ritonavir, fosamprenavir, darunavir, atazanavir (including the sulfate salt), and nelfinavir (including the mesylate salt);
16) a nucleoside or nucleotide reverse transcriptase inhibitor optionally selected from lamivudine, emtricitabine, abacavir, zalcitabine, zidovudine, tenofovir (including tenofovir disoproxil fumarate), didanosine, and stavudine;
17) a non-nucleoside reverse transcriptase inhibitor optionally selected from delavirdine, efavirenz and nevirapine;
18) a fixed dose combination optionally selected from Atripla, Combivir, Trizivir and Truvada;
19) an entry inhibitor (such as a fusion inhibitor or CCR5 co-receptor antagonist) optionally selected from maraviroc and enfuvirtide; and
20) an integrase inhibitor such as raltegravir (MK-0518) or elvitegravir (GS-9137).

Where an additional anti-HIV agent is used it optionally may be in another form, such as a salt, solvate, hydrate, prodrug form, polymorph, enantiomer and the like. The additional anti-HIV agent also may be selected from:
21) a nucleoside reverse transcriptase inhibitor optionally selected from amdoxovir, apricitabine, and elvucitabine;
22) a protease inhibitor which is optionally brecanivir or GS-8374;
23) a CCR5 Receptor antagonist optionally selected from Aplaviroc, PRO2000 and Vicriviroc;
24) a non-nucleoside reverse transcriptase inhibitor which is optionally Etravirine (TMC-125), Rilpivirine (TMC-278), or Calanolide A;
25) an integrase inhibitor which is optionally Elvitegravir, GSK-364735 or raltegravir; and:
 a maturation inhibitor that is optionally Bevirimat (PA457);
 a cellular inhibitor, such as hydroxyurea;
 an entry inhibitor, such as vicriviroc or TNX-355; and
 an immune based inhibitor such as Immunitin (alpha-epibromide), proleukin (IL-2), Remune (HIV-1 immunogen), BAY 50-4798 or IR103.

Hosts, including humans, infected with a virus or any other condition described herein, can be treated by administering to the patient an effective amount of the active ingredient. For subjects with multiple drug resistance, the active ingredient can be administered either alone or in combination with one or more other therapeutic agents. The active compounds may be administered by any appropriate route, for example, orally, parenterally, enterally, intravenously, intradermally, subcutaneously, percutaneously, transdermally, intranasally, topically or by inhalation therapy, and may be in solid, liquid or vapor form.

The active ingredient(s) in one embodiment are administered in an amount sufficient to deliver to a patient a therapeutically effective amount of the active compound in order to e.g., inhibit viral infection, without causing serious toxic effects in a treated subject. An "inhibitory amount" includes an amount of active ingredient sufficient to halt viral replication as measured by, for example, an assay such as the ones referred to herein.

A typical dose of the compound may be in the range of from about 1 to about 50 mg/kg, from about 1 to about 20 mg/kg, of body weight per day, more generally from about 0.1 to about 100 mg/kg body weight of the recipient per day. Lower dosages may be used, for example, doses of about 0.5-100 mg, 0.5-10 mg, or 0.5-5 mg per kilogram body weight per day. Even lower doses may be useful, and thus ranges can include from about 0.1-0.5 mg/kg body weight of the recipient per day. The effective dosage range of the pharmaceutically acceptable derivatives is calculated based on the weight of the parent indole derivative compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose or preferably as divided doses throughout a day. In particular embodiments, the compound or composition is administered four times per day. In particular embodiments, the compound or composition is administered three times per day. In particular embodiments, the compound or composition is administered two times per day. In particular embodiments, the compound or composition is administered once per day.

In one embodiment, the active ingredient is administered to achieve peak plasma concentrations of the active compound of from about 0.02 to 70 µM, or from about 0.5 to 10 µM. For example, this can be achieved by intravenous injection of a 0.1 to 5% solution of active ingredient, optionally in saline, or administered as a bolus of active ingredient. It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

One mode of administration of the active compound is oral. Oral compositions usually include an inert diluent or an edible carrier. They may be enclosed in gelatin capsules, compressed into tablets, or delivered in liquid form. For oral therapeutic administration, the active compound may be incorporated with excipients or formulated as solid dispersions or solid solutions, and used in the form of tablets, troches, or capsules. By a "solid dispersion" is meant a solid state comprising at least two components where one component is dispersed more or less evenly throughout the other component. By "solid solution" is meant a solid state comprising at least two components that are chemically and physically integrated to produce a homogeneous product. A solid solution is typical over a solid dispersion because it more easily forms a liquid solution upon contact with an appropriate liquid medium, thereby increasing the bioavailability of a drug. Pharmaceutically compatible binding agents and/or adjuvant materials also may be included as part of this composition.

7. EXAMPLES

7.1 Instruments and General Procedures

7.1.1. Microscopy

A Zeiss Universal microscope configured with a polarized visible light source and polarizable analyzer was used to evaluate the optical properties of the samples. Specimens were typically mounted on a microscope slide with a drop of immersion oil and a cover glass. Magnification was typically 100×. Observations of particle/crystal size and shape were recorded. The presence of birefringence was also noted.

7.1.2. Molecular Spectroscopy—$^1$H-NMR

Samples were prepared by dissolving 1-10 mg in dimethylsulfoxide (DMSO)-$d_6$ with 0.05% (v/v) tetramethylsilane (TMS). Spectra were collected at ambient temperature on a Varian Gemini 400 MHz FT-NMR spectrometer.

7.1.3. Differential Scanning Calorimetry (DSC)

DSC data were collected on a TA Instruments 2910 DSC. In general, samples in the mass range of 1 to 10 mg were crimped in aluminum sample pans and scanned from 25 to about 250° C. or 300° C. at 10° C./minute using a nitrogen purge at 50 mL/min.

7.1.4. Thermogravimetric Analysis (TGA)

TGA data were collected on a TA Instruments 2950 TGA. In general, samples in the mass range of 5 to 15 mg were placed in an open, pre-tared platinum sample pan and scanned from 25 to about 300° C. at 10° C./minute using a nitrogen purge at 100 mL/min.

7.1.5. Hot Stage Microscopy (HSM)

A Zeiss Universal microscope configured with a polarized visible light source and a Mettler hot stage accessory was used. Specimens were mounted on a microscope slide with a drop of immersion oil and a cover glass. Magnification was typically 100×. Samples were heated from 25° C. to about 200° C. at 3 or 10° C./minute Linksys 32 temperature control and data capture software system (Linkam Scientific Instruments Ltd, Waterfield, Tadworth, Surrey KT20 5LR, UK). Observations of phase change, recrystallization, evolution of bubbles, etc. were recorded.

7.1.6. Infrared Spectroscopy (FTIR)

For infrared analysis, the samples were analyzed without further preparation. Infrared spectra were obtained with a Nicolet 510 M-O Fourier transform infrared spectrometer, equipped with a Harrick Splitpea™ attenuated total reflectance device. A portion of the sample was placed on the crystal of the nanosampler and approximately 2 lb force was applied with the pressure applicator. Spectra were acquired from 4000-400 cm$^{-1}$ with a resolution of 4 cm$^{-1}$, and 128 scans were collected for each analysis.

7.1.7. X-Ray Powder Diffraction (XRD)

X-ray powder diffraction patterns were obtained using a Bruker D8 Discovery diffractometer equipped with an XYZ stage, laser video microscope for positioning, and a two dimensional HiStar area Detector. Collection times were nominally 60 seconds. A Cu K-alpha radiation 1.5406 angstrom source operating at 40 kV and 40 mA was used to irradiate samples. The X-ray optics consists of a Gobel mirror coupled with a pinhole collimator of 0.5 mm. Theta-theta continuous scans were employed with a sample-detector distance of 14.97 or 14.975 cm, which gives an effective 2-theta range of 4-40 degrees. Samples were mounted in low background quartz plates. A variable temperature hot stage was used to manipulate sample temperature for some experiments. In general, depending upon sample preparation, data collection temperature, and other variables, the position of a particular characteristic X-ray powder diffraction peak may be expected to shift by as much as about 0.2 degrees 2-theta, or, in some cases, up to about 0.3 degrees 2-theta, as understood in the art.

7.1.8. Solubility

Milligram size quantities of each sample were placed into a vial. Solvent was added and the vials were vortexed for a few minutes, followed by visual observation for remaining solids. The solvent was incrementally added until the solids were dissolved, or a maximum volume of solvent was added and the experiment was terminated. Parallel to that, a suspension is made and filtered, the solids was examined by XRD to determine if a phase transformation occurs.

7.1.9. Hygroscopicity—Dynamic Vapor Sorption (DVS)

(Performed by Surface Measurement Systems Ltd., Allentown, Pa.)

Form I was run in an automated dynamic vapor sorption analyzer. The sample was dried in vacuum and then scanned by placing the samples into the instrument and running dry air over them until they no longer lost mass at 0% RH. The samples were subjected to 0 to 95% RH back to 0% RH at 25° C. in 5% RH steps.

7.1.10. Chiral Purity by HPLC Total Area Normalization

HPLC-TAN was used to evaluate the chiral purity of samples assigned as Form I, Form VIII, and Form IX. The ratio between enantiomers of R and S was determined. Area normalization was used to calculate the chromatographic chiral purity based on both enantiomers. Total area normalization assumed that both enantiomers had a uniform response factor.

The equipment used was high performance liquid chromatography (HPLC) system with binary gradient capability with mobile phase isopropyl alcohol/methyl alcohol/trifluoroacetic acid (75:25:0.0375 vol.). Five microliters of prepared samples with about 0.3 mg/mL was injected to a Chiralpak AD-H column. The flow rate was 0.4 mL/min. The sample was detected at 235 nm by UV. The A/S Flush was isopropanol:methanol 75:25 vol.

7.1.11. Moisture by Karl Fischer (KF)

The analysis for water was performed using KF titrimetry. Both volumetric and coulometric titrations were used for different samples. Brinkmann 716 DMS Titrino was used in volumetric titration and Mitsubishi Moisturemeter CA-100 was used in coulometric titration. The sample (7-11 mg) was accurately weighed and quickly transferred to the titration vessel before measuring the water content.

7.2 Example 1

Polymorph Screening Results

The compound 2-carbamoyl-5-chloro-1H-indol-3-yl)-[3-((E)-2-cyano-vinyl)-5-methyl-phenyl]-(R)-phosphinic acid methyl ester was contacted with several potential solvent systems. Resulting solid forms were observed as shown in Table 1.

TABLE 1

Summary of Polymorphic Forms

| Form Designation | Description |
|---|---|
| Form I | Anhydrate |
| Form VIII | Monohydrate |
| Form IX | Anhydrate |

The different form designations shown in Table 1 include a monohydrate and two anhydrous crystalline forms.

Another lowly ordered form (Form III) was slurried in water and methanol and was observed to convert to Form I in methanol and Form VIII in water Annealing of Form III for 14 days at 46° C. revealed no change in the XRD pattern indicative of increased crystallinity.

The characteristics of the monohydrate form (Form VIII) were studied. The dehydration behavior was explored using heat. The experiments led to conversion of the nicely crystalline monohydrate to a lowly ordered material (Form III) which liquefied and crystallized as Form I with additional heating. This suggests that dehydration may initially lead to a lowly ordered or completely disordered solids depending on the conditions used.

Dehydration of Form VIII was also studied using competitive slurry experiments in methanol/water solvent systems (bridging experiments) suggesting that the critical water activity level for Form I/Form VIII interconversion is around 40-60 vol % water. While dehydration using heat yielded lowly ordered materials, conversion of Form VIII to an anhydrous crystalline form occurs when the hydrate is slurried in organic solvents below the critical water activity level.

The hydration behavior of Form I was explored. In general, Form I was practically insoluble in neat water and did not show changes in XRD pattern when slurried in water at both ambient temperature and 50° C. for up to 6 days. This suggests Form I is slow to convert to Form VIII without seeding even when above the critical water activity level. When seeds of Form VIII were present (as in a competitive slurry), Form I was readily observed to transform into Form VIII. This indicates that once Form VIII nucleates (which is expected above the critical water activity level), the batch would be expected to convert to Form VIII.

Form IX has the lowest solubility among Forms I, VIII and IX at ambient temperature (in dry 2-butanol). Form IX was initially isolated during a competitive slurry experiment of Form I and Form VIII. The low yield of Form IX from this experiment suggests that the Form IX material was isolated simply due to the preferential dissolution of Forms I and VIII (the Form I material contained residual Form IX).

The slurry experiment of Form I and Form IX in non aqueous solvent yielded Form IX suggesting Form IX is a more thermodynamically stable form.

In general, (2-carbamoyl-5-chloro-1H-indol-3-yl)-[3-((E)-2-cyano-vinyl)-5-methyl-phenyl]-(R)-phosphinic acid methyl ester exhibits two anhydrous polymorphic forms (Forms I and IX), one monohydrate (Form VIII) and several solvated forms and lowly ordered forms. Both the anhydrous forms and hydrate exhibit low solubility in water.

Form IX is the most stable form under ambient temperature and pressure. While it is the most thermodynamically stable form identified during the study, it was difficult to get Form IX to crystallize.

Form I can convert to the monohydrate (Form VIII) when exposed to high water activity levels. Therefore, Form I solids should in one embodiment be protected from moisture.

7.3 Example 2

X-Ray Powder Diffraction (XRD) Data

An XRD was obtained of (2-carbamoyl-5-chloro-1H-indol-3-yl)-[3-((E)-2-cyano-vinyl)-5-methyl-phenyl]-(R)-phosphinic acid methyl ester Form I and is shown in FIG. 1A. FIG. 4A shows a second type of XRD pattern for (2-carbamoyl-5-chloro-1H-indol-3-yl)-[3-((E)-2-cyano-vinyl)-5-methyl-phenyl]-(R)-phosphinic acid methyl ester Form III. FIG. 3A shows the pattern for (2-carbamoyl-5-chloro-1H-indol-3-yl)-[3-((E)-2-cyano-vinyl)-5-methyl-phenyl]-(R)-phosphinic acid methyl ester Form VIII. FIG. 2A shows the pattern for (2-carbamoyl-5-chloro-1H-indol-3-yl)-[3-((E)-2-cyano-vinyl)-5-methyl-phenyl]-(R)-phosphinic acid methyl ester Form IX.

An additional representative XRD pattern of Form I is shown in FIG. 5. This pattern was collected using a step size of 0.02 degrees 2-theta and a time per step of 4 s. A summary of XRPD angles and calculated lattice spacing characteristic of Form I is given in Table 2.

TABLE 2

X-ray diffraction peak information for Form I.

| Angle 2-Theta ° | d value Angstrom | Intensity Count | Intensity % % |
|---|---|---|---|
| 7.203 | 12.2633 | 19.6 | 45.9 |
| 9.289 | 9.51324 | 31.4 | 73.5 |
| 9.624 | 9.18309 | 20.4 | 47.9 |
| 10.628 | 8.31754 | 15.3 | 35.8 |
| 11.297 | 7.82611 | 18.7 | 43.7 |
| 11.6 | 7.62278 | 15.2 | 35.7 |
| 12.092 | 7.31332 | 18.1 | 42.3 |
| 13.766 | 6.42769 | 21.6 | 50.7 |
| 14.435 | 6.13107 | 24.2 | 56.7 |
| 15.481 | 5.71908 | 13.9 | 32.6 |
| 16.653 | 5.31928 | 13.9 | 32.6 |
| 18.635 | 4.75781 | 11.2 | 26.3 |
| 19.221 | 4.61399 | 14.8 | 34.6 |
| 19.954 | 4.44616 | 16.2 | 37.9 |
| 20.854 | 4.2562 | 16.9 | 39.6 |

TABLE 2-continued

X-ray diffraction peak information for Form I.

| Angle 2-Theta ° | d value Angstrom | Intensity Count | Intensity % % |
|---|---|---|---|
| 21.276 | 4.17266 | 33.7 | 79.1 |
| 21.758 | 4.08146 | 42.7 | 100 |
| 22.634 | 3.92539 | 13.9 | 32.7 |
| 22.99 | 3.86541 | 14.4 | 33.8 |
| 23.262 | 3.8208 | 18.4 | 43.2 |
| 23.829 | 3.73118 | 28.2 | 66.1 |
| 24.832 | 3.58262 | 15.4 | 36 |
| 25.481 | 3.49281 | 15.8 | 37.1 |
| 26.109 | 3.41024 | 25.5 | 59.8 |
| 27.845 | 3.2014 | 15.1 | 35.3 |

An additional representative XRD pattern of Form VIII is shown in FIG. 6. This pattern was collected using a step size of 0.01 degrees 2-theta and a time per step of 6 s. A summary of the XRPD angles and calculated lattice spacing characteristic of the Form I is given in Table 3.

7.4 Example 3

Thermal Behavior

The thermal behavior of Form I was determined by differential scanning calorimetry and thermogravimetric analysis. The DSC thermogram of Form I batch exhibited multiple thermal events. A small endotherm began near 116° C. (about 1 J/g) followed by a broad exotherm starting at 153° C. (11 J/g) followed by a sharp endotherm at 213° C. (86 J/g). The final endotherm was attributed to melting. The sample begins decomposing shortly after melting, and the total weight loss at 240° C. was about 0.7 wt %. FIG. 1B shows an overlay of DSC and TGA thermograms.

TABLE 3

X-ray diffraction peak information for Form VIII.

| Angle 2-Theta ° | d value Angstrom | Intensity Count | Intensity % % |
|---|---|---|---|
| 6.707 | 13.16806 | 243 | 21.8 |
| 9.424 | 9.37658 | 48.6 | 4.4 |
| 10.246 | 8.62628 | 26.2 | 2.3 |
| 10.883 | 8.12333 | 46.7 | 4.2 |
| 11.36 | 7.78314 | 41.1 | 3.7 |
| 13.401 | 6.60182 | 331 | 29.6 |
| 17.166 | 5.16155 | 52.3 | 4.7 |
| 17.736 | 4.99693 | 57.9 | 5.2 |
| 20.214 | 4.38944 | 1115 | 100 |
| 21.792 | 4.07515 | 59.8 | 5.4 |
| 22.839 | 3.89061 | 41.1 | 3.7 |
| 24.364 | 3.65047 | 33.4 | 3 |
| 25.347 | 3.51104 | 35.2 | 3.2 |

Variable temperature X-ray diffraction (vtXRD) experiments on Form I were performed to aid in characterizing the thermal behavior. A sample of Form I was heated in an XRD camera from 25° C. to 225° C. The diffraction pattern of Form I exhibited little change until around 225° C., where the sample melted. The small thermal events that were observed from 115° C. to 170° C. using DSC were not observed using vtXRD. FIG. 1C shows the vtXRD stacked plot diffractograms showing their consistent structure as a function of temperature.

The thermal behavior of Form III was determined by differential scanning calorimetry and thermogravimetric analysis. The DSC thermogram of Form III exhibited similar thermal events as Form I, except the small events were much more pronounced. The small endotherm began near 116° C. (about 4 J/g), followed by a broad recrystallization exotherm starting at 165° C. (65 J/g) and a sharp melting endotherm at 212° C. (82 J/g). TGA shows a total weight loss of 0.7 wt % at 240° C. The XRD, DSC and TGA data indicate that this sample was a partially amorphous (and partially crystalline) anhydrous material. FIG. 4B shows an overlay plot of the DSC and TGA thermograms.

Variable temperature x-ray diffraction experiments on Form III were performed to help characterize the material behavior. The sample was heated in the XRD unit from 25° C. to 180° C. The XRD pattern revealed a decrease in the intensity of the major peak at 20.4° 2θ at 110° C., eventually became totally amorphous. The samples became translucent and liquefied at this temperature. Cooling the sample back to 50° C. resulted in crystallization of Form I. These changes further explained the DSC thermal events. The sample turned slowly into amorphous at around 115° C. as observed in DSC thermogram as an endothermic peak, and eventually melted and recrystallized at 170° C. FIG. 4C shows the overlay plot of the vtXRD diffractograms. Hot stage microscopy data provided vivid evidence of the thermal changes upon heating of this sample. The sample was heated at 20° C./min, image was taken at about every 6 degrees. The solids were birefringent using polarized light microscopy. From about 87° C. to 122° C., some particles shifted slightly from original position. At 125° C., the solids started to lose birefringence and slowly melted. The sample almost all melted by about 174° C., then started slowly recrystallizing from the melt. The recrystallized solids melted at about 224° C.

A ripening experiment was done on Form III material in neat methanol in an effort to improve the degree of crystallinity of the sample. Excess Form III was placed in the above solvent for about 1 day at ambient temperature and the solids were filtered to collect XRD data. Form III material converted to Form I under these experimental conditions. Non-competitive slurries of Form III in water for 3 days resulted in Form VIII.

The thermal behavior of Form VIII was examined by differential scanning calorimetry and thermogravimetric analysis. The DSC thermogram of Form VIII exhibited multiple endotherms. A broad endotherm starting above 105° C. (113 J/g) corresponded with a TGA weight loss of approximately 4 wt %, this corresponds to about 1 mole of water. An endotherm at 169° C. (65 J/g) was attributed to the recrystallization of the sample. The endothermic region near 213° C. was attributed to melting of the recrystallized sample. The sample achieved constant weight after dehydration and eventually decomposed above 240° C. FIG. 3B shows an overlay of the DSC and TGA thermograms.

Hot stage micrographs of Form VIII were taken. The sample was mounted in silicone oil and heated from 25° C. at 10° C. per minute. Similar as Form III sample, the particles started to shift their position at about 82° C. The evolution of bubbles in the range of 125 to 140° C. was noted indicating the evolution of volatiles which corresponded with the broad DSC endotherm and TGA weight loss. The majority of the sample liquefied in the process of dehydration, taking into account the high enthalpy (113 J/g) value involved in this process, suggesting water molecules may play an important role in the crystal structure. The sample then slowly recrystallized from the melt in the range from 144° C. to 198° C. The bulk of the sample melted at 214° C., however, some residue crystalline material didn't melt even at 254° C.

Variable temperature x-ray diffraction experiments on Form VIII were performed to help characterize the thermal behavior. The sample was heated in the XRD unit from 25° C. to 185° C. The sample started to lose peak intensity at about 75° C. and became totally amorphous in the range of 120 to 150° C. At 160° C., the pattern of Form I was observed indicating that, after dehydration, the sample recrystalized as Form I. The observations in HSM and XRD coincided with a DSC endotherm and TGA weight loss. FIG. 3C shows the overlay XRD diffractograms.

7.5 Example 4

7.5.1. Solvent Recrystallization

Material was solvent recrystallized under approximately 100 different crystal growth conditions. The scale of the recrystallization experiments was approximately 15 mL. The primary means of changing the crystal growth conditions was accomplished by using variable solvents. The saturation temperature, growth temperature, and evaporation rate (relative supersaturation) were also varied to create additional differences in crystal growth conditions.

Saturated solutions were prepared by agitating excess test material in contact with the various solvent systems at the saturation temperature. The mother liquor was separated from the residual solids by filtration. The mother liquor was then heated above the saturation temperature (overheated) to dissolve any remaining solids. The temperature of the solutions was then adjusted to the growth temperature and a controlled nitrogen shear flow was introduced to begin solvent evaporation.

Overall, the polymorph screen was divided into five different recrystallization panels. The desaturation conditions for the five panels are summarized in Table 4. The wells within each panel contained different solvent compositions. Because of the different solvent composition in each well, each well acted as a different crystal growth experiment. The compositional solvent matrices for the five recrystallization panels used during the solvent-based portion of the polymorph screen are shown in TABLES 5 to 9.

Solids generated from the four recrystallization panels were analyzed by powder XRD along with samples generated by other means such as slurry experiments. To mitigate the preferred grain effects, a two dimensional detection system was used to collect all the XRD screening data. The two dimensional detector integrates along the concentric Debye cones which helps reduce pattern variation.

TABLE 4

Summary of Solvent Based Recrystallization Panels

| Panel | No. of wells | Solids (mg) | Scale (mL) | Saturation Temp. (° C.) | Overheat Temp. (° C.) | Growth Temp. (° C.) | N₂ Flow Rate (psi) |
|---|---|---|---|---|---|---|---|
| I | 26 | 40 | 15 | 25 | 35 | 25 | 0.5 |
| II | 26 | 40 | 15 | 45 | 65 | 55 | 0.5 |
| III | 24 | 40 | 15 | 25 | 40 | 25 | 0.5 |

TABLE 4-continued

Summary of Solvent Based Recrystallization Panels

| Panel | No. of wells | Solids (mg) | Scale (mL) | Saturation Temp. (° C.) | Overheat Temp. (° C.) | Growth Temp. (° C.) | N₂ Flow Rate (psi) |
|---|---|---|---|---|---|---|---|
| IV | 18 | 100 | 4-15 | 40 | 55 | 40 | 0 |
| V | 4 | 50-200 | 3-60 | 25 | 40 | 25 | 0.5 |

TABLE 5

Recrystallization Panel 1:

| Well | Solvent | Solubility (mg/mL) | Recrystallized Solids | XRD Group |
|---|---|---|---|---|
| 1 | methanol | 10 | white solids | I and a few II |
| 2 | ethanol | 3.64 | white solids | I |
| 4 | 2-propanol | <2.67 | white solids | I |
| 5 | 1-propanol | ~2.67 | white solids | I |
| 6 | 2-butanol | <2.67 | Glass and white solids | I |
| 14 | nitromethane | 5.71 | Glass and white solids | I |

TABLE 6

Recrystallization Panel 2:

| Well | Solvent | Recrystallized solids | XRD Group |
|---|---|---|---|
| 2 | ethanol | glass and white solids | I |
| 4 | 2-propanol | glass and white solids | I |
| 5 | 1-propanol | glass and white solids | I |
| 6 | 2-butanol | glass and white solids | I |
| 7 | 1-butanol | glass and white solids | I |
| 17 | isopropyl ether | white solids | II and I |

TABLE 7

Recrystallization Panel 3:

| Solvent | | 1 | 2 | 3 | Co/AntiSolvent |
|---|---|---|---|---|---|
| MeCl₂ | A | 12:3 | 7.5:7.5 | 3:12 | 2-propanol |
| EtOH | B | 12:3 | 7.5:7.5 | 3:12 | water |
| acetone | C | 12:3 | 7.5:7.5 | 3:12 | 1-propanol |
| acetonitrile | D | 12:3 | 7.5:7.5 | 3:12 | ethyl acetate |
| trifluoroethanol | E | 12:3 | 7.5:7.5 | 3:12 | THF |
| DMF | F | 12:3 | 7.5:7.5 | 3:12 | acetonitrile |
| MeOH | G | 12:3 | 7.5:7.5 | 3:12 | chloroform |
| EtOH | H | 12:3 | 7.5:7.5 | 3:12 | toluene |
| MeCl₂ | A | amorphous | amorphous | I and amorphous | 2-propanol |
| EtOH | B | III and amorphous | III and amorphous | II | water |
| acetone | C | amorphous | amorphous | amorphous | 1-propanol |
| acetonitrile | D | low order I | amorphous | II and amorphous | ethyl acetate |
| trifluoroethanol | E | NA | NA | NA | THF |
| DMF | F | II and amorphous | NA | NA | acetonitrile |
| MeOH | G | III and amorphous | III and amorphous | II and amorphous | chloroform |
| EtOH | H | II and amorphous | V | V | toluene |

Note:
NA means no XRD experiment was conducted

TABLE 8

Recrystallization Panel 4:

| Well | Solvent | Solvent Volume (mL) | Recrystallized solids | XRD Group |
|---|---|---|---|---|
| 1 | methanol | 8 | white solids | I |
| 2 | Ethanol | 11 | white solids | I |
| 10 | ethyl acetate | 4 | white solids | I |
| 11 | methyl ethyl ketone (MEK) | 15 | white solids | I |
| 13 | acetonitrile | 4 | white solids | I |

Note:
1) the starting solid is 100 mg in each well.

TABLE 9

Recrystallization Panel 5:

| Well | Solvent | Solids (mg) | Solvent Volume (mL) | Recrystallized solids | XRD Group |
|---|---|---|---|---|---|
| 2 | ethanol:water (3:12 v/v) | 200 | 60 | waxy look soft film | II |

7.6 Example 5

Noncompetitive Slurry Experiments

Noncompetitive slurry experiments were performed. These experiments rely on solubility differences of different polymorphic forms (if the compound exists in different polymorphic forms). As such, only polymorphs having a lower solubility (more stable) than the original crystalline form can result from a noncompetitive slurry experiment.

Essentially, when a solid is dissolved in a (slurry) solvent, a saturated solution eventually results. The solution is saturated with respect to the polymorphic form dissolved. However, the solution is supersaturated with respect to any polymorphic form which is more stable (more stable forms have lower solubility) than the polymorphic form initially dissolved. Therefore, any of the more stable polymorphic forms can nucleate and precipitate from solution. In addition, non-competitive slurry experiments are often useful in identifying solvents that form solvates with the compound.

The slurry experiments were performed by exposing excess "starting" material to neat solvents and agitating the resulting suspensions for approximately 1 week at ambient temperature. The solids were mechanically filtered and analyzed by XRD to determine the resulting form. To avoid possible desolvation or physical change after isolation, the samples were not subjected to drying before X-ray analysis.

The summary of non-competitive slurry experiments are shown in Table 10.

TABLE 10

Non-competitive Slurry Experiment

| Experiment | Solvent | XRD |
|---|---|---|
| 1 | methanol | I |
| 2 | 1-propanol | I |
| 3 | ethanol | I |
| 4 | 2-butanol | I |
| 5 | 1-butanol | I |
| 6 | water | I |
| 7 | nitromethane | I |
| 8 | isopropyl ether | I |
| 9 | isopropyl acetate | I |
| 10 | acetonitrile | I |
| 11 | toluene | IV |
| 12 | water (50° C.) | I |

Note:
The slurry experiment was conducted under ambient temperature except for experiment number 12. Samples were slurried for at least 7 days before XRD testing.

Additional non-competitive slurry experiments were performed by suspending a particular polymorphic form with a solvent system and agitating the suspension isothermally. The non-competitive slurry experiments were used in attempts to identify the critical water activity levels for the interconversion of Form I (anhydrate target form) and Form VIII (monohydrate form). This was used to identify the water content range that can be used during processing to successfully isolate Form I in a reproducible manner. In each non-competitive slurry experiment, an excess of Form I of known weight was added to a water-methanol mixture. The suspension was slurred at ambient temperature (22° C.) continuously for up to 12 days in order to obtain thermodynamic equilibrium. Excess solids were collected at different slurry times by centrifugation, and then characterized by XRD. To avoid possible desolvation or physical change after isolation, the samples were not subjected to drying before X-ray analysis. The results are summarized in Table 11.

TABLE 11

Form I Non-competitive Slurry Experiment at 22° C.

| Initial Form | Water (wt %) | Slurry duration (Days) | Final Forms |
|---|---|---|---|
| I | 84 | 3 | I |
| I | 70 | 3 | I |
| I | 66 | 3 | I |

TABLE 11-continued

Form I Non-competitive Slurry Experiment at 22° C.

| Initial Form | Water (wt %) | Slurry duration (Days) | Final Forms |
|---|---|---|---|
| I | 61 | 3 | I |
| I | 56 | 3 | I |
| I | 51 | 3 | I |
| I | 46 | 5 | I |
| I | 41 | 5 | I |
| I | 24 | 5 | I |

7.7 Example 6

Competitive Slurry Experiments

Competitive slurry experiments were performed by mixing excess amounts of the polymorphic forms together in different solvents and agitating isothermally. These types of slurry experiments were used in attempts to determine which phase is more thermodynamically stable under the conditions used.

The slurry results are summarized in Table 12. Slurry experiments were generally used to examine the energy relationship between Form I and Form IX, and to examine how these two forms may interconvert with the monohydrate (Form VIII).

A competitive slurry of Form I and IX was observed to convert to Form IX (in 2-butanol) suggesting that Form IX is a more thermodynamically stable form (relative to Form I).

Form I converted to Form VIII in neat water during a competitive slurry experiment. Form IX was also slurried in water, but remained unchanged in water for several days. These data indicated that Form I is susceptible to formation of the hydrate while Form IX appeared to be less susceptible. This may be attributable to the lower solubility of Form IX which may affect the solvent mediated transformation kinetics. The solubility of Form I and Form VIII may be very similar, which would also reduce the rate of transformation between these two forms.

Bridging experiments were performed on Form I and VIII in a gradient of water and methanol. The mixtures of Form I and Form VIII were observed to convert to Form VIII in methanol/water 1:4 and 2:3 (v:v) solvent systems, and converted to Form I in methanol/water 3:2 (v:v). This suggests the critical water activity for hydration of Form I is approximately 40% to 50% water level. However, there was one experiment (methanol/water 4:1 system) in which the mixture is converted to the hydrate which was outside of this range. This outcome may have resulted due to the limited amounts of solids used during these experiments. Form I has a higher solubility in the solvent systems relative to Form VIII as indicated by solubility measurements.

The amount of solids of Form I may have all dissolved leaving only solids of Form VIII in the system.

To investigate this possibility, a less soluble solvent, ethanol was chosen. The mixture converted to Form I in the ethanol/water 9:1 (v:v) system, which was consistent with results using pure methanol solvent.

TABLE 12

Competitive Slurry Experiments

| Initial Forms | Solvent | Slurry duration | Final Forms |
|---|---|---|---|
| I & VIII | water | 3 days | VIII |
| I & VIII | methanol | 3 days | I |
| I & VIII | methanol/water volume ratio 1:4 | 3 day | VIII |
| I & VIII | methanol/water volume ratio 2:3 | 3 day | VIII |
| I & VIII | methanol/water volume ratio 3:2 | 3 days | I |
| I & VIII | methanol/water volume ratio 4:1 | 3 days | VIII |
| I & VIII | methanol/water volume ratio 9:1 | 6 days | I |
| VIII & IX | water | 5 days | VIII & IX |
| VIII & IX | 2-butanol | 5 days | IX |
| I & IX | 2-butanol | 6 days | IX |

These experiments demonstrate that Form I can be typically crystallized from a methanol water solution in which the methanol is in excess. Typically if water is in excess of methanol then Form VIII may form.

Additional competitive slurry experiments were performed by mixing excess amounts of polymorphic forms in a solvent system and agitating the mixture isothermally. The competitive slurry experiments were used in attempts to identify the critical water activity levels for the interconversion of Form I (anhydrate target form) and Form VIII (monohydrate form). This was used to identify the water content range that can be used during processing to successfully isolate Form I in a reproducible manner. In each competitive slurry experiment, an excess of Form I and Form VIII of known weight was added to a water-methanol mixture. The suspension was slurred at ambient temperature (22° C.) or 45° C. continuously for up to 12 days in order to obtain thermodynamic equilibrium. Excess solids were collected at different slurry times by centrifugation, and then characterized by XRD. To avoid possible desolvation or physical change after isolation, the samples were not subjected to drying before X-ray analysis. The results are summarized in Tables 13 to 17.

TABLE 13

Form I/Form VIII Competitive Slurry Experiments at 22° C. Overnight

| Initial Forms | Water (wt %) | Final Forms |
|---|---|---|
| I & VIII | 84 | VIII |
| I & VIII | 70 | VIII |
| I & VIII | 66 | I + VIII |
| I & VIII | 61 | I + VIII |
| I & VIII | 56 | I + VIII |
| I & VIII | 51 | I + VIII |
| I & VIII | 46 | I + VIII |
| I & VIII | 41 | I + VIII |
| I & VIII | 24 | I |

TABLE 14

Form I/Form VIII Competitive Slurry Experiments at 22° C. for 5 Days

| Initial Forms | Water (wt %) | Final Forms |
|---|---|---|
| I & VIII | 84 | VIII |
| I & VIII | 70 | VIII |
| I & VIII | 66 | VIII |
| I & VIII | 61 | VIII |
| I & VIII | 56 | VIII |
| I & VIII | 51 | I + VIII |
| I & VIII | 46 | I + VIII |
| I & VIII | 41 | I + VIII |
| I & VIII | 24 | I |

TABLE 15

Form I/Form VIII Competitive Slurry Experiments at 22° C. for 12 Days

| Initial Forms | Water (wt %) | Final Forms |
|---|---|---|
| I & VIII | 84 | VIII |
| I & VIII | 70 | VIII |
| I & VIII | 66 | VIII |
| I & VIII | 61 | VIII |
| I & VIII | 56 | VIII |
| I & VIII | 51 | VIII |
| I & VIII | 46 | I + VIII |
| I & VIII | 41 | I + VIII |
| I & VIII | 24 | I |

TABLE 16

Form I/Form VIII Competitive Slurry Experiments at 45° C. Overnight

| Initial Forms | Water (wt %) | Final Forms |
|---|---|---|
| I & VIII | 84 | VIII |
| I & VIII | 70 | I + VIII |
| I & VIII | 66 | I + VIII |
| I & VIII | 61 | I + VIII |
| I & VIII | 56 | I + VIII |
| I & VIII | 51 | I |
| I & VIII | 46 | I |
| I & VIII | 41 | I |
| I & VIII | 24 | I |

TABLE 17

Form I/Form VIII Competitive Slurry Experiments at 45° C. for 12 Days

| Initial Forms | Water (wt %) | Final Forms |
|---|---|---|
| I & VIII | 84 | I |
| I & VIII | 70 | I |
| I & VIII | 66 | I |
| I & VIII | 61 | I |
| I & VIII | 56 | I |
| I & VIII | 51 | I |
| I & VIII | 46 | I |
| I & VIII | 41 | I |
| I & VIII | 24 | I |

7.8 Example 7

Water Antisolvent Experiments

Form I solids were dissolved in pure methanol, filtered, and a known amount of water was added stepwise until solids precipitated. Water was added slowly to avoid adding more water than necessary and to avoid localized regions of high supersaturation. The total amount of water added to bring about precipitation was recorded.

The solids were collected and characterized by XRD to determine their polymorphic form. The results are summarized in Table 18.

TABLE 18

Water Antisolvent Experiments

| Form I* (mg) | Methanol (mL) | Water Added (mL) | Water (wt %) | Results |
|---|---|---|---|---|
| 100 | 11.3 | 3.3 | 26.8 | No precipitate |
| 100 | 11.3 | 3.3 | 26.8 | No precipitate |
| 100 | 10.6 | 3.5 | 29.2 | VIII |
| 100 | 10.6 | 3.2 | 27.4 | VIII |
| 100 | 10 | 3 | 27.4 | VIII |
| 100 | 10 | 3.5 | 30.4 | VIII |
| 60 | 8.1 | 3 | 30 | VIII |
| 60 | 8.1 | 3 | 30 | VIII |

*Value shown is the original amount added in pure methanol before filtration.

The water antisolvent experiments indicated that at least 27 wt % water was needed to precipitate solids under the loading and temperature used. The solids that precipitated were all determined to be Form VIII (monohydrate). These data were consistent with the competitive slurry experiments suggesting that a water content level of 24 wt % or below is need to stabilize Form I (anhydrate).

7.9 Example 8

Methanol Stripping Study

Methanol stripping was performed using a MTBE:THF solution of the compound of Formula I. The results are summarized in Table 19.

TABLE 19

Methanol Stripping Experiments

| Trial | Scale (mL) | Sample Temperature (° C.) | Times of Methanol Stripping | Solids Precipitated at Step | Final Form | Final Water Content (wt %) |
|---|---|---|---|---|---|---|
| 1 | 20 | Not measured | 4× | 2× | VIII | 9.3 |
| 2 | 20 | 0-16 | 1× | 1×* | VIII | NA |
| 3 | 10 | 16-22 | 3× | 3× | VIII | 7.5 |

*Solution was stripped to near dryness.

All three trials yielded Form VIII (monohydrate) solids. The water content of the resulting slurry was 9.3 wt % (Trial 1) and 7.5 wt % (Trial 3) based on KF analysis. It was very difficult to control the solution temperature during evaporation at such small scale, as a result, the temperature varied considerably during these experiments and was lower than the desired target temperature (35-40° C.). The final water content reported in Table V may be slightly less than the water content of the solution when the first solids appeared.

7.10 Example 9

Processes for preparing (2-carbamoyl-5-chloro-1H-indol-3-yl)-[3-((E)-2-cyano-vinyl)-5-methyl-phenyl]-(R)-phosphinic acid methyl ester including isomers and salts thereof are described in U.S. patent application Ser. No. 11/229,150, filed Sep. 16, 2005; PCT WO 2006/054182, published May 26, 2006; U.S. patent application Ser. No. 11/906,095, filed Sep. 28, 2007; PCT US2007/020900, filed Sep. 28, 2007; and U.S. Prov. Appl. No. 60/932,713, filed May 31, 2007; the disclosures of each of which are incorporated herein by reference in their entirety.

7.11 Example 10

Other Analytical Data 7.11.1. Annealing Experiments

In addition to the solvent recrystallization experiments and slurry experiments, annealing experiments were performed. These experiments entailed looking for structural changes as a function of temperature. This was accomplished by using variable-temperature XRD, and variable temperature ovens, and DSC experiments.

7.11.2. Hydration Experiments

Hydration experiments were performed on (2-carbamoyl-5-chloro-1H-indol-3-yl)-[3-((E)-2-cyano-vinyl)-5-methyl-phenyl]-(R)-phosphinic acid methyl ester Form III sample. A known weight of sample was exposed to a 95% RH environment using a saturated solution of sodium chloride. After 18 days of exposure to 95% RH, the sample exhibited no changes in XRD pattern.

7.11.3. Dynamic Vapor Sorption (2-carbamoyl-5-chloro-1H-indol-3-yl)-[3-((E)-2-cyano-vinyl)-5-methyl-phenyl]-(R)-phosphinic acid methyl ester Form I was analyzed by dynamic moisture sorption desorption analysis in an effort to understand how the different forms respond to ambient moisture. The sample was dried in vacuum and then scanned by placing the samples into the instrument and running dry air over them until they no longer lost mass at 0% RH. The sample was subjected to 0 to 95% RH back to 0% RH at 25° C. in 5% RH steps.

7.11.4. Solubility Experiments

Solubility experiments were performed to determine the solubility of the different polymorphic forms. The most stable form would have the lowest solubility. Solubility data were collected on polymorphs I, VIII, and IX. Two of the forms were anhydrous and one was hydrated. Since the preliminary data suggested that the solubility of all three forms in water is very low, to improve the accuracy of the experiment, the solubility experiments were performed in dry 2-butanol at ambient temperature, as it gives higher apparent solubility.

Excess solids were placed in a test tube, solvent was then added in the tube, vortexed, and examined visually to determine if all the solids had dissolved. Attempts were made to prepare saturated or nearly saturated solutions of each polymorphic form by exposing excess solids of each polymorph to dry 2-butanol.

The XRD pattern of the undissolved solids suggested that Form I did not undergo solvent-mediated transformation during the solubility experiment. Form VIII also kept the majority of its XRD pattern after the solubility experiment (a hydrate would be expected to eventually undergo dehydration in anhydrous solvent). There were sample limitations with Form IX, so no XRD data were collected on the undissolved solids of Form IX during the solubility determinations.

Table 20 suggests that Form I has the highest solubility of the three forms tested. Form I appears to be a less stable from than Forms VIII and IX under the test conditions. Form IX appeared to be the least soluble form in 2-butanol, although its solubility is in the same range as Form VIII, suggesting that Form IX is the most stable form under the conditions.

According to the XRD, it is possible that some amount of Form VIII started to transform (perhaps to anhydrous material), however, the majority of the sample was still perceived to be Form VIII.

The solubility data suggest that the hydrate form (Form VIII) has higher solubility than the stable anhydrous form (Form IX), although this phenomenon occurs infrequent, it is not uncommon. Our competitive slurry experiment further confirmed these conclusions.

TABLE 20

Apparent Kinetic Solubility in 2-butanol of Different Crystalline Forms at 25° C.

| Form | Solubility (mg/mL) |
| --- | --- |
| I | 1.81 |
| VIII | 0.31 |
| IX | 0.16 |

The solubility data suggest that Form IX is a more stable polymorphic form. Form VIII (the monohydrate) appears to have a lower solubility than Form I, suggesting that if the water activity level of the reaction mass is sufficiently high, it is likely that conversion to Form VIII would occur.

7.11.5. Fourier-Transform Infrared Spectroscopy (FTIR)

FIGS. 7 and 8 provide representative FTIR spectra for Form I. FIGS. 9, 10, and 11 provide representative XRPD spectra for Form VIII. Table 21 provides some of the characteristic vibrational bands for Forms I and VIII. Locations of characteristic peaks from different samples of a given crystal form are provided to exemplify variation that may exist among certain samples of a given crystal form.

TABLE 21

FTIR Spectral Features of Form I and Form VIII

| Form I (cm$^{-1}$) Sample 1, Sample 2 | Form VIII (cm$^{-1}$) Sample 1, Sample 2, Sample 3 |
| --- | --- |
| 3286, 3284 | 3294, 3301, 3292 |
| 3068, 3063 | 3146, 3147, 3130 |
| 2951, 2951 | 2948, 2949, 2949 |
| 2816, 2814 | 2843, 2844, 2844 |
| 2221, 2220 | 2218, 2219, 2218 |
| 1679, 1679 | 1668, 1680, 1670 |
| 1619, 1619 | 1621, 1623, 1620 |
| 1403, 1403 | 1411, 1412, 1410 |
| 1195, 1195 | 1184, 1184, 1179 |
| 1010, 1010 | 1020, 1019, 1021 |

7.11.6. Chiral HPLC Analysis

Chiral analysis was performed on Form IX to determine its chiral composition. Form IX material was prepared by stirring about two grams each of Form I and form VIII in 75 mL of pure methanol for 2 days. About 30 milligrams of solids were obtained by centrifuging the solution. The XRD analysis confirmed that the isolated material was Form IX with residual Form VIII.

Form I, Form VIII, and Form XI were analyzed by chiral HPLC. The results are summarized in Table 22.

TABLE 22

Chiral HPLC Analysis Results

| Sample | R Isomer (%) | S Isomer (%) |
| --- | --- | --- |
| Form I | 99.5 | 0.51 |
| Form VIII | 98.5 | 1.55 |
| Form IX | 64.6 | 35.44 |

All publications and patent applications cited in this specification are herein incorporated by reference as if each individual publication or patent application were specifically and individually indicated to be incorporated by reference. This disclosure has been described with reference to certain embodiments. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims. Variations and modifications of the disclosure, will be obvious to those skilled in the art from the foregoing detailed description of the disclosure.

The disclosure will be understood by the following non-limiting claims.

What is claimed is:

1. A crystal form of (2-carbamoyl-5-chloro-1H-indol-3-yl)-[3-((E)-2-cyano-vinyl)-5-methyl-phenyl]-(R)-phosphinic acid methyl ester.

2. The crystal form of claim 1 that is anhydrous.

3. The crystal form of claim 1, which exhibits an X-ray powder diffraction peak at about 21.8° 2θ.

4. The crystal form of claim 1, which exhibits an X-ray powder diffraction peak at about 9.3° 2θ.

5. The crystal form of claim 1, which exhibits X-ray powder diffraction peaks at about 21.3, 23.8, and 26.1° 2θ.

6. The crystal form of claim 1, which substantially corresponds to the X-ray powder diffraction pattern of FIG. 1A.

7. The crystal form of claim 1, which substantially corresponds to the X-ray powder diffraction pattern of FIG. 5.

8. The crystal form of claim 1, which exhibits a differential scanning calorimetry endotherm with an onset temperature of about 213° C.

9. The crystal form of claim 1, which exhibits a thermal gravimetric analysis weight loss of less than about 1.0% of the total mass when heated from about 25° C. to about 219° C.

10. The crystal form of claim 1, which exhibits infrared spectroscopy peaks at about 3284 and 3063 cm$^{-1}$.

11. The crystal form of claim 1, which exhibits infrared spectroscopy peaks at about 1619 and 1010 cm$^{-1}$.

12. The crystal form of claim 1, which corresponds to the infrared spectrum of FIG. 7.

13. The crystal form of claim 1, which corresponds to the infrared spectrum of FIG. 8.

14. The crystal form of claim 1, which comprises water.

15. The crystal form of claim 1, which is a monohydrate.

16. The crystal form of claim 1, which exhibits an X-ray powder diffraction peak at about 20.2° 2θ.

17. The crystal form of claim 1, which exhibits an X-ray powder diffraction peak at about 13.4° 2θ.

18. The crystal form of claim 1, which exhibits X-ray powder diffraction peaks at about 6.7, 9.4, and 21.8° 2θ.

19. The crystal form of claim 1, which substantially corresponds to the X-ray powder diffraction pattern of FIG. 3A.

20. The crystal form of claim 1, which substantially corresponds to the X-ray powder diffraction pattern of FIG. 6.

21. The crystal form of claim 1, which exhibits a differential scanning calorimetry endotherm with an onset temperature of about 105° C.

22. The crystal form of claim 1, which exhibits a differential scanning calorimetry endotherm with an onset temperature of about 213° C.

23. The crystal form of claim 1, which exhibits a thermal gravimetric analysis weight loss of between about 3% and about 5% of the total mass when heated from about 25° C. to about 120° C.

24. The crystal form of claim 1, which exhibits infrared spectroscopy peaks at about 3301 and 3147 cm$^{-1}$.

25. The crystal form of claim 1, which exhibits infrared spectroscopy peaks at about 1623 and 1019 cm$^{-1}$.

26. The crystal form of claim 1, which substantially corresponds to the infrared spectrum of FIG. 9.

27. The crystal form of claim 1, which substantially corresponds to the infrared spectrum of FIG. 10.

28. The crystal form of claim 1, which substantially corresponds to the infrared spectrum of FIG. 11.

29. A process for preparing the crystal form of claim 1 comprising the step of crystallizing (2-carbamoyl-5-chloro-1H-indol-3-yl)-[3-((E)-2-cyano-vinyl)-5-methyl-phenyl]-(R)-phosphinic acid methyl ester in an alcoholic solvent.

30. The process of claim 29, wherein the alcoholic solvent is an excess of methanol in water.

31. The process of claim 29, wherein the alcoholic solvent comprises methanol.

32. A crystal form of a mixture of R and S isomers of (2-carbamoyl-5-chloro-1H-indol-3-yl)-[3-((E)-2-cyano-vinyl)-5-methyl-phenyl]phosphinic acid methyl ester.

33. The crystal form of claim 32 that is anhydrous.

34. The crystal form of claim 32, which exhibits an X-ray powder diffraction peak at about 22.7° 2θ.

35. The crystal form of claim 32, which exhibits an X-ray powder diffraction peak at about 11.8° 2θ.

36. The crystal form of claim 32, which exhibits X-ray powder diffraction peaks at about 6.9 and 22.3° 2θ.

37. The crystal form of claim 32, which substantially corresponds to the X-ray powder diffraction pattern of FIG. 2A.

38. The crystal form of claim 32, which exhibits no substantial thermal events between about 25 and 247° C., as measured by differential scanning calorimetry.

39. The crystal form of claim 32, which exhibits a thermal gravimetric analysis weight loss of less than about 1.0% of the total mass when heated from about 25° C. to about 200° C.

40. A pharmaceutical composition comprising the crystal form of claim 1 and one or more pharmaceutically acceptable carriers, excipients, or diluents.

41. The pharmaceutical composition of claim 40, wherein the crystal form is a pure form.

42. The pharmaceutical composition of claim 40, wherein the composition is provided in a solid oral dosage form.

43. The pharmaceutical composition of claim 40, wherein the composition further comprises emtricitabine and tenofovir disoproxil fumarate.

44. A method of treating an HIV infection, comprising administering the pharmaceutical composition of claim 40.

45. The method of claim 44, wherein the method further comprises administering an active agent.

46. The method of claim 45, wherein the active agent is a combination of emtricitabine and tenofovir disoproxil fumarate.

* * * * *